(12) United States Patent
Buersgens et al.

(10) Patent No.: US 10,544,450 B2
(45) Date of Patent: Jan. 28, 2020

(54) METHOD FOR DUPLICATING NUCLEIC ACIDS BY MEANS OF A POLYMERASE CHAIN REACTION

(71) Applicant: GNA Biosolutions GmbH, Planegg/Martinsried (DE)

(72) Inventors: Federico Buersgens, Planegg/Martinsried (DE); Joachim Stehr, Planegg/Martinsried (DE); Lars Ullerich, Planegg/Martinsried (DE)

(73) Assignee: GNA Biosolutions GmbH, Planegg/Martinsried (DE)

( * ) Notice: Subject to any disclaimer, the term of this patent is extended or adjusted under 35 U.S.C. 154(b) by 111 days.

(21) Appl. No.: 15/524,864

(22) PCT Filed: Nov. 7, 2014

(86) PCT No.: PCT/EP2014/074101
§ 371 (c)(1),
(2) Date: May 5, 2017

(87) PCT Pub. No.: WO2016/070945
PCT Pub. Date: May 12, 2016

(65) Prior Publication Data
US 2018/0237842 A1    Aug. 23, 2018

(51) Int. Cl.
*C12P 19/34* (2006.01)
*C12Q 1/6844* (2018.01)

(52) U.S. Cl.
CPC ..... *C12Q 1/6844* (2013.01); *C12Q 2523/313* (2013.01); *C12Q 2527/113* (2013.01); *C12Q 2563/155* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 8,003,370 B2 * | 8/2011 | Maltezos | B01L 3/50851 435/283.1 |
| 2002/0061588 A1 | 5/2002 | Jacobson et al. | |
| 2003/0143604 A1 | 7/2003 | Storhoff et al. | |
| 2011/0039305 A1 * | 2/2011 | Termaat | B01L 7/52 435/91.2 |
| 2011/0262912 A1 * | 10/2011 | Tonnigahara | C12Q 1/683 435/6.11 |
| 2015/0118715 A1 * | 4/2015 | Wittwer | B01L 7/52 435/91.2 |
| 2016/0289736 A1 * | 10/2016 | Jones | B01L 7/525 |

FOREIGN PATENT DOCUMENTS

| | | |
|---|---|---|
| AU | 201480964 A1 | 12/2014 |
| DE | 102013215166 B3 | 10/2014 |
| EP | 1842924 B1 | 6/2009 |
| WO | WO-2007143034 A1 | 12/2007 |
| WO | WO-2013/113910 A1 | 8/2013 |

* cited by examiner

*Primary Examiner* — Kenneth R Horlick
(74) *Attorney, Agent, or Firm* — Harris Beach PLLC; Laura W. Smalley

(57) ABSTRACT

The invention relates to a method for the duplication of nucleic acids by means of a polymerase chain reaction, in the case of which a cycle consisting of the steps of denaturing, annealing and elongation is repeatedly performed. In one embodiment, the yield (g) of specimens of a nucleic acid to be duplicated, at the end of at least one passage of the cycle, is less than 80 percent of the specimens of the nucleic acid present at the beginning of said passage and, in the case of at least one passage of the cycle, the reaction time (tA) is less than one second. In addition, in a further embodiment, the number (k) of passages of the cycle of the polymerase chain reaction is greater than 45 and/or in at least one of the passage the cycle time tc is less than 20 seconds.

14 Claims, 6 Drawing Sheets

Specification includes a Sequence Listing.

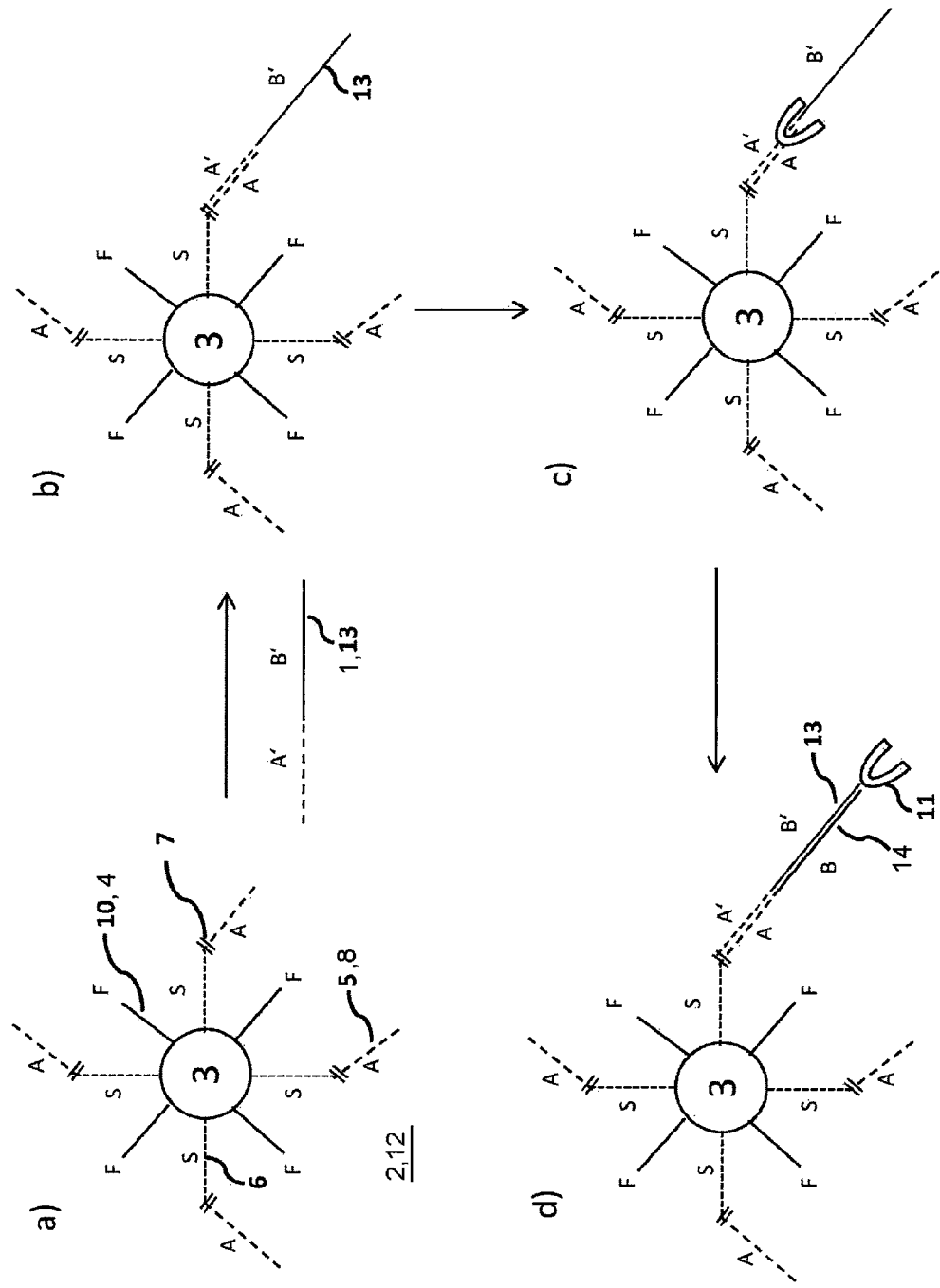

SEQUENCE LISTING

```
<160> NUMBER OF SEQ ID NOS: 6

<210> SEQ ID NO 1
<211> LENGTH: 54
<212> TYPE: DNA
<213> ORGANISM: Artificial Sequence
<220> FEATURE:
<223> OTHER INFORMATION: Engineered sequence
<220> FEATURE:
<221> NAME/KEY: misc_feature
<222> LOCATION: (35)..(36)
<223> OTHER INFORMATION: 2 abasic modification spacer9 molecules
```

-continued positioned between position 35 and position 36

<400> SEQUENCE: 1
aaaaaaaaaa aaaaaaaaaa aaaaaaaaaa aaaaagttca ggcacagcac atca    54

<210> SEQ ID NO 2
<211> LENGTH: 22
<212> TYPE: DNA
<213> ORGANISM: Artificial Sequence
<220> FEATURE:
<223> OTHER INFORMATION: Engineered sequence

<400> SEQUENCE: 2
gctcacaccg ataccatcag cg                                        22

<210> SEQ ID NO 3
<211> LENGTH: 59
<212> TYPE: DNA
<213> ORGANISM: Artificial Sequence
<220> FEATURE:
<223> OTHER INFORMATION: Engineered sequence

<400> SEQUENCE: 3
tgcgacgctc acaccgatac catcagcgat ctctttgatg tgctgtgcct gaaccgtta    59

<210> SEQ ID NO 4
<211> LENGTH: 21
<212> TYPE: DNA
<213> ORGANISM: Artificial Sequence
<220> FEATURE:
<223> OTHER INFORMATION: Engineered sequence

<400> SEQUENCE: 4
catgcctgca cccgttccac c                                         21

<210> SEQ ID NO 5
<211> LENGTH: 19
<212> TYPE: DNA
<213> ORGANISM: Artificial Sequence
<220> FEATURE:
<223> OTHER INFORMATION: Engineered sequence

<400> SEQUENCE: 5
gttcaggcac agcacatca                                            19

<210> SEQ ID NO 6
<211> LENGTH: 20
<212> TYPE: DNA
<213> ORGANISM: Artificial Sequence
<220> FEATURE:
<223> OTHER INFORMATION: Engineered sequence

<400> SEQUENCE: 6
cgctcacacc gataccatca                                           20

METHOD FOR DUPLICATING NUCLEIC ACIDS BY MEANS OF A POLYMERASE CHAIN REACTION

This application is a national stage application under 35 U.S.C. § 371 of PCT Application No. PCT/EP2014/074101, filed Nov. 7, 2014.

FIELD OF THE INVENTION

The invention relates to a method for the amplification of nucleic acids by means of a polymerase chain reaction (PCR).

BACKGROUND OF THE INVENTION

PCR methods are known from the prior art. The patent specification U.S. Pat. No. 4,683,202 B1 discloses a method, with which at least one specific nucleic acid sequence contained in a nucleic acid or a mixture of nucleic acids can be amplified, wherein each nucleic acid consists of two separate, complementary strands, of equal or unequal length. The method comprises: (a) treating the strands with two primers for each different specific sequence being amplified under such conditions that, for each different sequence being amplified, an extension product for each primer is synthesized, which is complementary to the respective nucleic acid strand. Said primers are selected so that they are substantially complementary to different strands of each specific sequence, so that the extension product that is synthesized from a primer can be used, if separated from its complement, as a template for the synthesis of the extension product of the other primer; (b) separating the primer extension products from the templates, on which they were synthesized so that single-stranded molecules are produced; (c) treating the single-stranded molecules from step (b) with the primers from step (a) under such conditions that a primer extension product is synthesized, wherein each of the single strands of step (b) is used as a template. The steps can be carried out one after the other or simultaneously. In addition the steps (b) and (c) can be repeated until the desired degree of sequence amplification is achieved.

In the international application laid open for public inspection WO 2007/143034 A1, methods are disclosed that are to be suitable for performing a PCR method. The methods may include the use of an optical radiation source for heating in a PCR method. The methods may also include the use of surface plasmon resonance or fluorescence resonance energy transfer for monitoring a PCR method in real-time. The methods may further include the immobilization of a template, primer or a polymerase on a surface such as gold or another surface that is active in relation to the surface plasmon resonance.

The patent application US 2002/0061588 A1 discloses methods for making nucleic acids locally and directly responsive to an external signal. The signal acts only on one or a plurality of specific localized portions of the nucleic acid. According to the invention the signal can change the properties of a specific nucleic acid and thereby also change its function. Accordingly the invention provides methods for regulating the structure and functioning of a nucleic acid in a biological sample without influencing other constituent parts of the sample. In one embodiment a modulator transfers heat to a nucleic acid or a part of a nucleic acid, which results e.g. in intermolecular or intramolecular bonds being destabilized, and the structure and stability of the nucleic acid changing. Preferred modulators include metal nanoparticles, semiconductor nanoparticles, magnetic nanoparticles, oxide nanoparticles and chromophores. It is also proposed to use these methods in association with a PCR method. It is proposed in particular to control a PCR reaction with a modulator.

The patent application DE 10 2012 201 475 A1 relates to a method for the amplification of nucleic acids. In this method, electromagnetically excited nanoparticles in a reaction volume transfer heat to their environment through excitation. If the heat input is below a critical duration, which depends on the average particle distance in the solution and thus the concentration of the nanoparticles, a very rapid denaturing can be achieved, wherein the duration of the excitation of the nanoparticles is very much shorter than the cycle duration.

The patent DE 10 2013 215 166 B3 (publication date of the grant of patent: 30 Oct. 2014) of the inventors of this patent application contains a method for super-amplification, wherein the shortening of the cycle duration leads to a low yield per cycle, but which is more than compensated by the possibility of being able to perform more cycles per time unit.

The patent application US 2003/0143604 A1 relates to the use of nanoparticle detection probes for monitoring amplification reactions, in particular PCR. The patent application deals primarily with the use of nanoparticle-oligonucleotide conjugates which are treated with a protective reagent such as bovine serum albumen, in order to detect a target polynucleotide quantitatively and qualitatively. The patent application discloses a nucleic acid amplification and detection using gold nanoparticle primers. In a first step the nucleic acid target is denatured in the presence of the gold nanoparticles, to which primers are attached. In a second step the gold nanoparticles hybridize with the primers attached thereto to the nucleic acid target and a copy of the complementary DNA sequence is produced based on the nucleic acid primers which are attached to the nanoparticles. The first and second steps are repeated and the optical signal which is produced through the binding of complementary nanoparticle probes that have been amplified is measured.

The patent specification EP 1 842 924 B1 discloses a method for determining an initial concentration of nucleic acids using nucleic acid real-time amplification data, wherein a measured fluorescence, due to the amplification, passes through a function dependent on the number of cycles passed through.

Object of the Invention

It is the object of the invention to provide an improved method for the amplification of nucleic acids by means of a polymerase chain reaction (PCR). It is in particular the object to facilitate a more rapid and/or greater amplification of nucleic acids by means of a PCR.

Solution According to the Invention

The object is achieved according to the invention by a method for the amplification of nucleic acids by means of a polymerase chain reaction (PCR), wherein a cycle consisting of the steps: denaturing, annealing and elongation is performed repeatedly.

The solution of the object is accomplished according to the invention furthermore by a method for the amplification of nucleic acids by means of a PCR, wherein a cycle consisting of the steps: denaturing, annealing and elongation is performed repeatedly, wherein the yield (g) of specimens of a nucleic acid to be amplified at the end of at least one of the passages of the cycle is less than 80% of the specimens of the nucleic acid present at the start of this passage of the cycle, and in at least one of the passages of the cycle a duration of effect ($t_A$) is shorter than one second.

The object is accomplished furthermore by a method for the amplification of nucleic acids by means of a PCR, wherein a cycle consisting of the steps: denaturing, annealing and elongation is repeatedly passed through, wherein the number (k) of the passages of the cycle of the polymerase chain reaction is greater than 45. In a PCR, a cycle that preferably includes, once in each case, the steps: denaturing, annealing (also referred to as hybridization) and elongation is repeatedly passed through and preferably in this sequence. In addition it is preferable for each of the steps to be of equal length in all passages of the cycle. However, this is by no means necessary. One or more of the steps in one passage of the cycle can, by all means, have a shorter duration than in another passage of the cycle. The duration $t_c$ of a passage of the cycle is referred to below as a cycle duration. The object according to the invention is achieved by a method for the amplification of nucleic acids by means of a PCR, wherein the cycle duration $t_c$ is less than 20 seconds in at least one passage of the cycle.

The object is achieved also by a method for the amplification of nucleic acids by means of a polymerase chain reaction, wherein a cycle consisting of the steps: denaturing, annealing and elongation is repeatedly passed through, wherein the cycle duration $t_c$ is reduced by the factor x with respect to the cycle duration of a reference polymerase chain reaction that is otherwise carried out identically, such that the yield (g) of specimens of a nucleic acid to be amplified at the end of at least one of the passages of the cycle is reduced, with respect to the yield of a reference PCR that is otherwise identically carried out, by the factor y, wherein the following applies: x>0.9y and g<80%.

A nucleic acid to be amplified is referred to below as an original. Another common term is "amplicon". The original is a single strand and can form, in the reaction volume, together with its complementary strand, which is described as a complement, a double strand. After each passage of the cycle a copy produced of the original is an original for the next passage of the cycle and a copy produced of the complement is a complement for the next passage of the cycle. In a passage of the cycle the number of specimens of the original and complement can be increased. The ratio of specimens of the original newly produced in one passage of the cycle to specimens of the original present directly before the cycle is described as the yield g of a passage of a cycle. In theory, in a PCR the number of originals per passage of the cycle can be doubled, thus a yield g of 100% achieved. In actual fact, however, the yield is generally less than 100%.

The cycle can be passed through repeatedly until the desired degree of amplification is reached. If, at the start of the PCR, $N_0$ original DNA molecules are contained in the reaction volume, and if g remains constant over the duration T of the whole PCR, hereinafter referred to as the process duration, $N_k$ DNA molecules with the sequence of the original are present in the reaction volume after k passages of the cycle:

$$N_k = N_0 * (1+g)^k. \qquad (1)$$

The yield g can be calculated as follows from the determination of the amplification factor $N_k/N_0$:

$$g = (N_k/N_0)^{1/k} - 1. \qquad (2)$$

For simplification, it is assumed here that the yield g per cycle remains constant during the PCR. In general, this assumption should apply in any case as long as no saturation effects arise, for example through the consumption of reaction partners.

The process duration T of the PCR that is required in order to reach a desired degree of amplification depends upon the duration of each passage of the cycle, hereinafter referred to as the cycle duration $t_c$, and also upon the yield. A long cycle duration also increases the process duration. However, a low yield also increases the process duration, because it requires more passages of the cycle.

The invention utilises, firstly, the fact that the yield that can be achieved in a passage of the cycle generally depends upon the cycle duration, to which the duration of effect $T_A$ substantially contributes. The theoretically achievable value of 100% yield per cycle thus requires that all originals successfully pass through all the steps of denaturing, annealing and elongation. This can no longer be ensured with an increasing shortening of the passage of the cycle, e.g. there may instead be only partial annealing or only partial elongation or only partial denaturing. The invention further utilises the finding of the inventors that the advantage of shortening the duration of a passage of a cycle can outweigh the disadvantage of a lower yield, in such a way that, despite the lower yield per passage of the cycle, the process duration required for a desired degree of amplification can be shortened.

The method according to the invention takes place in a chamber which is referred to below as the reaction volume. The reaction volume can be enclosed by a reaction vessel. The reaction volume contains a sample, in which usually the nucleic acid(s) to be amplified is/are present. The sample can include a liquid, preferably water. The cycles of the method according to the invention are passed through at least in a part of the sample. The liquid can advantageously serve as a suspension medium and/or solvent for the originals and complements and/or other constituent parts of the sample.

The denaturing step serves to denature a nucleic acid double strand, i.e. to separate it into its two single strands. For example, the original can be separated from the complement in the denaturing step. Denaturing is also referred to as melting. The denaturing of the nucleic acid double strand is usually thermally induced, i.e. at least a part of the nucleic acid double strand or the whole double strand is exposed to a temperature, described as a denaturing temperature, which causes or at least encourages a separation of the nucleic acid double strands. The denaturing temperature does not have to be a fixed temperature but can also be a temperature interval, within which the temperature in the denaturing step varies. The preferred denaturing temperature is selected on the one hand to be so high that nucleic acid double strands can be separated. On the other hand the preferred denaturing temperature is selected to be so low that a DNA polymerase, which is possibly also located in the sample, is not substantially damaged. A typical value for the denaturing temperature is 95° C.

The reaction volume further contains preferably at least two oligonucleotides, which are described as primers. One of these primers is described as a forward primer and another as a reverse primer. The forward primer is complementary to the 3'-end of the original. The reverse primer is complementary to the 3'-end of the complement. Annealing is understood to be the hybridization of the forward primers with the original and the reverse primers with the complement. The annealing step serves for the hybridization of the forward and reverse primers to their complementary sequences in the original or complement. The annealing is also usually thermally induced, i.e. at least a part of the original or the complement, or the whole original or the whole complement, is exposed to a temperature which is described as the annealing temperature, which causes or at least encourages a hybridization of the forward and reverse primers to their complementary sequences in the original or complement. Like the denaturing temperature, the annealing temperature can also be a temperature range, within which the temperature varies in the annealing step. The annealing step typically takes place at temperatures of 50° C. to 65° C. The annealing temperature is selected so that a hybridization of the primers that is as specific as possible can take place.

Hybridization means in the sense of the present invention the formation of a double strand from two single strands, which can each consist of a nucleic acid and/or an oligonucleotide. Under suitable reaction conditions the hybridization generally leads to the lowest possible energy state that can be achieved by the combination of the two single strands. In other words, under suitable conditions, the two single strands preferably bind to each other in such a way that, with respect to the sequences of the two single strands, the greatest possible complementarity (i.e. specificity) is produced.

If a nucleic acid A is partially complementary to a nucleic acid B, this means that the nucleic acid A is complementary in one part to a part of the nucleic acid B.

The terms "nucleic acid" and "oligonucleotide" include in the context of the present invention not only (desoxy)-ribonucleic acids and (desoxy)-oligoribonucleotides, but also nucleic acids and oligonucleotides that contain one or more nucleotide analogues with modifications on their backbone (e.g. methylphosphonates, phosphorothioates or peptic nucleic acids (PNA), in particular on a sugar of the backbone (e.g. 2'-O-alkyl derivatives, 3'- and/or 5'-aminoriboses, locked nucleic acids (LNA), hexitol nucleic acids, morpholinos, glycol nucleic acid (GNA), threose nucleic acid (TNA) or tricyclo-DNA—see in this connection the dissertation by D. Renneberg and C. J. Leumann, "Watson-Crick base-pairing properties of Tricyclo-DNA", J. Am. Chem. Soc., 2002, Volume 124, pages 5993-6002, of which the related content is part of the present disclosure through reference thereto) or that contain base analogues, e.g. 7-deazapurine or universal bases such as nitroindole or modified natural bases such as N4-ethyl-cytosine. In one embodiment of the invention the nucleic acids or oligonucleotides are conjugates or chimera with non-nucleoside analogues, e.g. PNA. The nucleic acids or oligonucleotides contain in one embodiment of the invention, at one or more positions, non-nucleoside units such as spacers, e.g. hexaethylene glycol or $C_n$-spacers with n between 3 and 6. If the nucleic acids or oligonucleotides contain modifications these are selected so that, also with the modification, hybridization with natural DNA/RNA analytes is possible. Preferred modifications influence the melt behaviour, preferably the melt temperature, in particular in order to be able to differentiate hybrids with different degrees of complementarity of their bases (mismatch discrimination). Preferred modifications include LNA, 8-aza-7-deazapurine, 5-propinyl-uracil and cytosine and/or abasic interruptions or modifications in the nucleic acid or in the oligonucleotide. Further modifications in the sense of the invention are, e.g., modifications with biotin, thiol and fluorescence donor and fluorescence acceptor molecules.

An abasic modification in the sense of the present invention is a portion of the oligonucleotide, in which the sequence of nucleotides is interrupted by the introduction of one or more molecules that do not constitute nucleotides, in such a way that a polymerase completely or partially interrupts the synthesis of an otherwise completely or partially hybridized, complementary oligonucleotide with respect to this portion, as there is insufficient base complementarity on this portion. An abasic modification is preferably selected from the group that includes: 1',2'-dideoxyribose (dSpacer), hexaethylene glycol (Spacer18) and triethylene glycol (Spacer9).

The reaction volume further contains preferably a DNA polymerase. The DNA polymerase can synthesize, in an elongation step starting from the forward primer, a copy of the complement. Starting from the reverse primer the DNA polymerase can synthesize a copy of the original. Through the synthesis the copy of the complement is hybridized with the original and the copy of the original is hybridized with the complement. For the purpose of elongation the DNA polymerase is exposed to a temperature, described as the elongation temperature, which allows or at least encourages an elongation. The elongation temperature can also be a temperature range, within which the temperature varies in the elongation step. When using a polymerase of *Thermus aquaticus* (Taq), an elongation temperature of 72° C. is typically used. In some embodiments of the PCR the annealing temperature and the elongation temperature are identical, i.e. both steps take place at the same temperature.

In a preferred embodiment, at least two steps of the PCR are performed at different temperatures, meaning that it may be necessary to provide one or more heating steps and/or cooling steps in the cycle, in which the reaction volume or parts of the reaction volume are heated or cooled. A heating or cooling step can take place before or after one of the steps of denaturing, annealing and elongation. A heating or cooling step thereby typically overlaps with the preceding and/or the subsequent denaturing, annealing or elongation step.

In the sense of the present invention the duration of effect $t_A$ of a passage of the cycle is the total duration, in which an energy source during the passage of the cycle acts on a point in the sample with a power suitable for denaturing in order to bring about heating in the sample.

The energy source transfers during the whole time $t_A$ a power suitable for denaturing to said point. An energy source in the form of a laser could be used for example with a higher power for denaturing and for a subsequent extinction measurement with lower power. In this case $t_A$ is merely the time, in which the laser transfers the higher power suitable for denaturing to the point.

If a plurality of energy sources are used for denaturing, $t_A$ preferably refers to the time, in which all energy sources for denaturing act simultaneously on the point. In the case of activation of a plurality of energy sources, frequently the denaturing will be achieved only with the simultaneous action.

Said point is thereby determined within the part of the sample, in which the method is carried out, so that $t_A$ assumes the greatest possible value. If therefore the heating is produced, for example, by a fixed Peltier element, $t_A$ is the total duration, in which heat flows from the Peltier element in this cycle to this point and brings about a temperature increase there that is suitable for denaturing (typically approximately the switch-on duration during the heating step; in any case shorter than the cycle duration). If the heating is produced by a light beam with the diameter d, which is guided (scanned) with a speed v through the sample volume, $t_A$ is the time duration $$\frac{d}{v},$$

during which the light beam hereby acts on a point in the sample with a power suitable for denaturing. If the heating is produced by a pulsed light source, of which the light beam is not moved relative to the sample during the pulse duration, the pulse duration is the duration of effect. If the heating is produced by a pulsed light source which is scanned through the sample, the shorter of the two durations (pulse duration and time duration $$\left.\frac{d}{v}\right)$$

is the duration of effect.

Through the selection according to the invention of particularly low values of the duration of effect $t_A$ and cycle duration $t_c$, a particularly rapid PCR method can be realised. In the case of a short duration of effect, numerous cycles can be passed through in a short time, so that a low yield can also be taken into account. Through the high number of cycles according to the invention, a greater amplification of the amplicon can advantageously be achieved.

Preferred Embodiments of the Invention

In a preferred embodiment of the invention a heating step takes place before the denaturing step, preferably overlapping with the denaturing step. In the heating step, the temperature in the denaturing step with respect to the temperature in the elongation step is increased preferably at least locally, i.e. in certain areas of the reaction volume, in order to facilitate denaturing. Through the effect of the energy source at least in these areas, preferably a temperature of at least 90° C., particularly preferably at least 95° C., is reached.

In a preferred embodiment of the invention a cooling step takes place before the annealing step, particularly preferably overlapping therewith, in order to reach the temperature required for annealing. If the temperature in the previous denaturing step was only locally increased, the cooling preferably takes place through heat diffusion in the reaction volume.

The part of the sample, in which the cycles of the method according to the invention are passed through, contains preferably at least 1%, particularly preferably at least 2%, particularly preferably at least 5%, particularly preferably at least 10% and more particularly preferably at least 20%, of the total sample volume. At the same time, said part preferably contains maximum 100%, particularly preferably maximum 80%, particularly preferably maximum 60% and more particularly preferably maximum 40%, of the total sample volume. An acceleration of the method can be achieved by the cycles being passed through in only a part of the sample.

The yield g of specimens of a nucleic acid to be amplified is preferably, at the end of at least one of the passages of the cycle—in a preferred embodiment of the invention at the end of each of 10, particularly preferably of each of 20, particularly preferably each of 40, particularly preferably each of 80, particularly each of 160 passages of the cycle— less than 70%, particularly preferably less than 60%, particularly preferably less than 50%, particularly preferably less than 40%, particularly preferably less than 30%, particularly preferably less than 20%, particularly preferably less than 10%, particularly preferably less than 5%, particularly preferably less than 2%, particularly preferably less than 1%, particularly preferably less than 0.5%, of the specimens of the nucleic acid present at the start of this passage of the cycle. This embodiment of the invention utilises the fact that, in particular in the case of particularly low yields, but still with a corresponding selection of the duration of a cycle, a particularly advantageous short process duration can be achieved.

The duration of effect $t_A$ in at least one of the passages of the cycle—in a preferred embodiment of the invention in at least 10 passages of the cycle, particularly preferably in at least 20, particularly preferably in at least 40, particularly preferably in at least 80, particularly preferably in at least 160 passages of the cycle—is preferably shorter than 10 s, particularly preferably shorter than 5 s, particularly preferably shorter than 3 s, particularly preferably shorter than 1 s, particularly preferably shorter than 500 ms (milliseconds), particularly preferably shorter than 250 ms, particularly preferably shorter than 100 ms, particularly preferably shorter than 50 ms, particularly preferably shorter than 25 ms, particularly preferably shorter than 10 ms, and more particularly preferably shorter than 8 ms, particularly preferably shorter than 3 ms, particularly preferably shorter than 1 ms, particularly preferably shorter than 500 µs, particularly preferably shorter than 300 µs, particularly preferably shorter than 100 µs, particularly preferably shorter than 50 µs, particularly preferably shorter than 30 µs, particularly preferably shorter than 10 µs. This embodiment of the invention utilises the fact that, in particular through a particularly short duration of effect $t_A$, a particularly advantageously short process duration can be achieved.

In a preferred embodiment of the invention, the yield g of specimens of a nucleic acid to be amplified is, at the end of at least one of the passages of the cycle—in a preferred embodiment of the invention at the end of each of 10 passages of the cycle, particularly preferably each of 20, particularly preferably each of 40, particularly preferably each of 80, particularly each of 160 passages of the cycle— less than 80%, less than 70%, less than 60%, less than 50%, less than 40%, less than 30%, particularly preferably less than 20% or 10%, particularly preferably less than 5%, particularly preferably less than 1%, of the specimens of the nucleic acid present at the start of this passage of the cycle, and, at the same time, in this passage or these passages of the cycle, the duration of effect $t_A$ is shorter than 5 seconds, particularly preferable shorter than 3 s, particularly preferably shorter than 1 s, particularly preferably shorter than 250 ms, particularly preferably shorter than 50 ms, particularly preferably shorter than 10 ms particularly preferably shorter than 3 ms, particularly preferably shorter than 1 ms, particularly preferably shorter than 300 µs, particularly preferably shorter than 100 µs, particularly preferably shorter than 30 µs, particularly preferably shorter than 10 µs. This embodiment of the invention utilises the fact that particularly advantageously short process durations can be achieved if a particularly low yield goes hand in hand with a particularly short duration of effect.

The yield g of specimens of a nucleic acid to be amplified is preferably, at the end of at least one of the passages of the cycle—in a preferred embodiment of the invention at the end of each of 10 passages of the cycle, particularly preferably each of 20, particularly preferably each of 40, particularly preferably each of 80, particularly preferably each of 160 passages of the cycle—more than 0.1%, particularly preferably more than 1%, particularly preferably more than 10%, of the specimens of the nucleic acid present at the start of this passage of the cycle. This embodiment of the invention utilises the fact that a yield that is not too low for each passage of the cycle can reduce the probability of errors in the amplification and can thus ensure a more reliable amplification result.

The duration of effect $t_A$ in at least one of the passages of the cycle—in a preferred embodiment of the invention in at least 10, particularly preferably in at least 20, particularly preferably in at least 40, particularly preferably in at least 80, particularly preferably in at least 160 passages of the cycle—is preferably longer than 1 µs, particularly preferably longer than 30 ps, particularly preferably longer than 100 ps, particularly preferably longer than 300 ps, particularly preferably longer than 1 ns, particularly preferably longer than 10 ns, particularly preferably longer than 100 ns, particularly preferably longer than 300 ns, particularly preferably longer than 1 ps, particularly preferably longer than 3 ps, particularly preferably longer than 10 µs. Through a moderate duration of effect, a more reliable denaturing can advantageously be achieved, in particular as the unravelling of a DNA double strand and a sufficient increase in the distance between the two strands through diffusion (to avoid re-hybridization), can require a sufficiently high temperature to be maintained for a certain time period of time.

In a preferred embodiment of the invention, the yield g of specimens of a nucleic acid to be amplified is, at the end of at least one of the passages of the cycle—in a preferred embodiment of the invention at the end of each of 10, particularly preferably each of 20, particularly preferably each of 40, particularly preferably each of 80, particularly each of 160 passages of the cycle—more than 0.1%, particularly preferably more than 1%, particularly preferably more than 10%, of the specimens of the nucleic acid present at the start of this passage of the cycle, and, at the same time, in this passage or these passages of the cycle the duration of effect $t_A$ is longer than 1 ps, particularly preferably longer than 30 ps, particularly preferably longer than 300 ps, particularly preferably longer than 1 ns, particularly preferably longer than 10 ns, particularly preferably longer than 100 ns, particularly preferably longer than 300 ns, particularly preferably longer than 1 µs, particularly preferably longer than 3 µs, particularly preferably longer than 10 µs, particularly preferably longer than 30 µs, particularly preferably longer than 100 µs, particularly preferably longer than 300 µs, particularly preferably longer than 1 ms, particularly preferably longer than 3 ms and more particularly preferably longer than 5 ms. This embodiment of the invention utilises the fact that a particularly more reliable amplification result can be achieved when a yield that is not too low goes hand in hand with a sufficiently long duration of effect.

The product $g \cdot t_c$ of the yield g and the cycle duration $t_c$ is described as the characteristic super-amplification time constant. This characteristic super-amplification time constant is preferably, at the end of at least one of the passages of the cycle—in a preferred embodiment at the end of each of 10, particularly preferably each of 20, particularly preferably each of 40, particularly preferably each of 80, particularly preferably each of 160 passages of the cycle—less than 20 s, particularly preferably less than 15 s, particularly preferably less than 12 s, particularly preferably less than 10 s, particularly preferably less than 8 s, particularly preferably less than 6 s, particularly preferably less than 4 s, particularly preferably less than 2 s. It is an achievable advantage of such embodiments of the invention that the PCR protocol is shortened. The invention is based on the idea that shorter cycle durations lead to a smaller increase per cycle, but this can be overcompensated, in the case of shortened duration of the whole protocol, by adding additional cycles.

According to the invention a cycle duration $t_c$—in a preferred embodiment each of 10, particularly preferably each of 20, particularly preferably each of 40, particularly preferably each of 80, particularly preferably each of 160 passages of the cycle—is selected, which is shortened by the cycle shortening factor x with respect to the cycle duration $t_{c_h}$ of an otherwise identically carried out reference PCR $$\left(\frac{t_{c_h}}{x} = t_c\right).$$

The reference PCR reaction is thereby in particular identical, with respect to the biochemical composition, the maintaining of the identical annealing, elongation and denaturing temperature and above all with respect to the target nucleic acid to be amplified and especially its sequence, concentration and pre-treatment. With the reference PCR, it is solely that the cycle duration is longer and the number of cycles may possibly be higher. This leads according to the invention to a yield per cycle g which, in comparison with the yield per cycle of the otherwise identically performed reference PCR, PIC $g_h$, is reduced by the efficiency loss factor PIC $$\left(\frac{g_h}{y} = g\right).$$

In one embodiment the following applies: x>0.9y, particularly preferably x=y, particularly preferably x>y, particularly preferably x>1.1y, particularly preferably x>1.2y, particularly preferably x>1.3y, particularly preferably x>1.5y, particularly preferably x>2y, particularly preferably x>2.5y, particularly preferably x>3y, particularly preferably x>5y, wherein at the same time it is preferably the case that x>1.2, particularly preferably x>1.5, particularly preferably x>2, particularly preferably x>2.5, particularly preferably x>3, particularly preferably x>4, particularly preferably x>5, particularly preferably x>10.

It can hereby be achieved that the "compound interest effect", which is facilitated by x times more cycles per time unit, more than compensates for the efficiency loss (i.e. by the yield per cycle reduced by the factor y) in the PCR according to the invention, i.e. that according to the invention more amplicon can be produced during a PCR of equal length or even a PCR of shorter length.

In the PCR according to the invention, more cycles are thereby preferably passed through than in the reference PCR, wherein the PCR according to the invention preferably passes through x times more cycles (x is the cycle shortening factor), particularly preferably 0.9× more, particularly preferably 0.8× more, particularly preferably 0.6× more, particularly preferably 0.4× more, particularly preferably 0.2× more cycles, and more particularly preferably 0.1× more cycles. It can hereby be achieved that the duration of the protocol is shorter than in the reference PCR, as the cycle duration is shortened by the cycle shortening factor x, but the number of required cycles and thus the duration of the whole protocol does not increase to the same extent.

In one embodiment the cycle shortening factor of the PCR according to the invention is, with respect to the reference PCR, preferably at least x>1.2, particularly preferably at least x>1.5, particularly preferably at least x>2, particularly preferably at least x>3, particularly preferably at least x>4, particularly preferably at least x>5, and more particularly preferably at least x>10. It can hereby be achieved that a significant "compound interest effect" or super-amplification effect arises.

For the solution according to the invention, the PCR must not yet have reached a saturation state, such as can arise, e.g. through the consumption of the limiting reactants (e.g. the primers or dNTPs), as such saturation effects can lead to a reduction in the yield per cycle in the course of the PCR. It is therefore provided in a preferred embodiment of the invention that the concentration of the limiting reactant, since the start of the PCR, has decreased by less than 80%, particularly preferably by less than 50%, particularly preferably by less than 25%, particularly preferably by less than 10%, particularly preferably by less than 5%, particularly preferably by less than 1%, particularly preferably by less than 0.1%.

It is also possible to ensure that saturation effects are avoided in that the yield per cycle is preferably extensively constant over the course of the PCR—in a preferred embodiment of the invention at the end of each of 10, particularly preferably each of 20, particularly preferably each of 40, particularly preferably each of 80, particularly preferably each of 160 passages of the cycle, is preferably still at least 95%, particularly preferably 90%, particularly preferably 80%, particularly preferably 70%, particularly preferably 50%, particularly preferably 20%, particularly preferably 10% of the yield of the cycle that had the highest yield during the PCR (typically the $1^{st}$ cycle).

Such saturation effects can also be avoided by limiting the solution according to the invention to preferably the first 80%, particularly preferably first 50%, particularly preferably first 25%, particularly preferably first 10%, of all passages of the cycle to be carried out in a PCR.

It is preferred that the number k of the passages of the cycle is greater than 45, particularly preferably greater than 50, particularly preferably greater than 60, particularly preferably greater than 70, particularly preferably greater than 80, particularly preferably greater than 90, particularly preferably greater than 100, particularly preferably greater than 120, particularly preferably greater than 160 and more particularly preferably greater than 200. Advantage is thereby taken of the fact that the positive effect of shortening the duration of the individual passages of the cycle becomes noticeable particularly when the number of passages is high.

The number k of the passages of the cycle is preferably less than 1000, particularly preferably less than 750 and more particularly preferably less than 500. Advantage is hereby taken of the fact that a number of passages that is not too high can have a positive effect on the reliability of the amplification result.

The abbreviations "M", "mM", "µM", "nM", "pM" and "fM", as given below, stand for the units: mol/l, mmol/l, pmol/l, nmol/l, pmol/l or fmol/l.

The concentration of the amplicon to be amplified is, at the start of the method, preferably greater than zero, preferably greater than $10^{-23}$ M (mol/l), particularly preferably greater than $10^{-21}$ M, particularly preferably greater than $10^{-20}$ M, particularly preferably greater than $10^{-19}$ M. It can advantageously be achieved through this embodiment of the invention that the amplification is sufficiently sensitive to produce an amount of amplification products that can be suitably detected.

The concentration of the amplicon to be amplified in the PCR is preferably less than 1 nM, particularly preferably less than 30 pM, particularly preferably less than 1 pM, particularly preferably less than 0.1 pM, particularly preferably less than 10 fM, particularly preferably less than 1 fM, particularly, preferably less than 0.1 fM. Through this embodiment of the method it is advantageously possible to prevent the amplification already reaching saturation before its end.

The number of amplicons to be amplified in the method is, at the start of the method, preferably less than 500,000, particularly preferably less than 200,000, particularly preferably less than 100,000, particularly preferably less than 10,000. Through this embodiment of the invention it is advantageously possible to prevent the amplification already reaching saturation before its end.

An important parameter of the invention can be the total duration $t_c$ of a passage of the cycle, thus the cycle duration. In particular it may be possible—despite a long duration of effect $t_A$- to achieve an advantageously short cycle duration by saving time at another point, e.g. a short annealing duration due to a high primer concentration in the sample or a short elongation time with the aid of a rapid DNA polymerase. The cycle duration $t_c$ is preferably in at least one of the passages of the cycle—in a preferred embodiment of the invention in at least 10, particularly preferably in at least 20, particularly preferably in at least 40, particularly preferably in at least 80, particularly preferably in at least 160 passages of the cycle, shorter than 40 s, particularly preferably shorter than 30 s, particularly preferably shorter than 20 s, particularly preferably shorter than 15 s, particularly preferably shorter than 12.5 s, particularly preferably shorter than 10 s, particularly preferably shorter than 7.5 s, particularly shorter than 5 s, particularly preferably shorter than 4 s, particularly preferably shorter than 3 s, particularly preferably shorter than 2 s and more particularly preferably shorter than 1 s.

On the other hand a passage of the cycle that is too fast can have a negative effect on the reliability of the amplification result. Therefore, in a preferred embodiment of the invention, the cycle duration $t_c$ preferably in at least one of the passages of the cycle—in a preferred embodiment of the invention in at least 10, particularly preferably in at least 20, particularly preferably in at least 40, particularly preferably in at least 80, particularly preferably in at least 160 passages of the cycle—is longer than 0.5 s, particularly preferably longer than 1 s, particularly preferably longer than 2 s, particularly preferably longer than 3 s, particularly preferably longer than 4 s, particularly preferably longer than 5 s.

The method according to the invention can advantageously be used in particular in larger volumes of samples, inter alia, because for statistical reasons a sufficient number of correct duplicates are still produced with greater reliability even with short cycle times. Preferably in at least one of the passages of the cycle—in a preferred embodiment of the invention in at least 10, particularly preferably in at least 20, particularly preferably in at least 40, particularly preferably in at least 80, particularly preferably in at least 160 passages of the cycle—the quotient $$\frac{t_A}{V_r}$$

of the duration of effect $t_A$ and the reaction volume $V_r$ irradiated by the energy source is less than 1 s/µl (seconds per microlitre), i.e. <1 s/µl, particularly preferably less than 0.1 s/µl, particularly preferably less than 0.01 s/µl and more particularly preferably less than 0.001 s/µl.

On the other hand it can be advantageous inter alia for the manageability of the method if in at least one of the passages of the cycle—in a preferred embodiment of the invention in at least 10, particularly preferably in at least 20, particularly preferably in at least 40, particularly preferably in at least 80, particularly preferably in at least 160 passages of the cycle—the quotient $t_A/V_r$ of the duration of effect $t_A$ and the reaction volume $V_r$ irradiated by the energy source is greater than 1 ps/µl, particularly preferably greater than 10 ps/µl, particularly preferably greater than 100 ps/µl, particularly preferably greater than 1 ns/µl, particularly preferably greater than 10 ns/µl and more particularly preferably greater than 100 ns/µl.

The energy source, which preferably produces global heating and, particularly preferably, local heating in the reaction volume is an electromagnetic radiation source, particularly preferably a light source, in a preferred method. A preferred light source emits light to heat the reaction volume preferably in the spectral range 200-2000 nm, particularly preferably in the range 300-1600 nm, particularly preferably in the range 300-1100 nm and most particularly preferably in the range 400-800 nm. The energy source is more particularly preferably a laser, e.g. a continuous or quasi-continuous diode laser or solid body laser or a nanosecond laser.

The invention is particularly well suited for the amplification of nucleic acids that are shorter than 2000 bases, particularly preferably shorter than 1000 bases, particularly preferably shorter than 300 bases, particularly preferably shorter than 200 bases, particularly preferably shorter than 150 bases, particularly preferably shorter than 100 bases, particularly preferably shorter than 80 bases, and more particularly preferably shorter than 60 bases. The amplicon to be amplified is preferably longer than 10 bases, particularly preferably longer than 30 bases and more particularly preferably longer than 50 bases. The method according to the invention can amplify DNA in said lengths particularly effectively.

Advantageously short cycle durations can be achieved, inter alia, by a rapid elongation. A DNA polymerase is preferably selected and the reaction conditions of the PCR set so that the DNA polymerase has a write speed of at least 1 base/s, particularly preferably at least 5 bases/s, particularly preferably at least 10 bases/s, particularly preferably at least 50 bases/s, particularly preferably at least 100 bases/s, particularly preferably at least 500 bases/s and more particularly preferably at least 1000 bases/s.

In a preferred embodiment of the invention nanoparticles in a reaction volume transfer heat to their environment through excitation. The nanoparticles are preferably particles which, due to their size, have particular optical properties, e.g. characteristic absorption or scattering spectra, which do not emerge, or do not emerge so clearly, in the volume material. The nanoparticles preferably have a diameter of between 2 and 500 nm (nanometres), particularly preferably between 3 and 300 nm and more particularly preferably between 5 and 200 nm. Preferred nanoparticles have a diameter of between 7 and 150 nm. The nanoparticles can be spherical, but in particular also non-globular forms, e.g. elongated nanoparticles (nanorods), can also be considered. In a preferred embodiment of the invention the nanoparticle comprises at least one semiconductor or a metal, preferably a precious metal, e.g. gold or silver. In one embodiment the nanoparticle consists completely of the metal, in another embodiment the metal forms only a part of the nanoparticle, e.g. its shell. A preferred nanoparticle may be a shell-core nanoparticle. A preferred nanoparticle may have pores at its surface, which may be occupied by atoms or molecules with a size and charge determined by the properties of the pores. These atoms or molecules particularly preferably attach themselves to the nanoparticle only when it is in a solution. According to the invention the nanoparticle also comprises the atoms and molecules taken up at its surface. Preferred nanoparticles are suited, due to their material absorption or plasmon resonance, for absorbing optical energy.

The heating time is the time that passes after the excitation intensity I(t) of the light source has reached its maximum value in the respectively excited volume until a temperature is set at each point in the excited volume that changes, even if the duration of effect is doubled, by maximum 3° C.

The cooling time is the time period after the switch-off point of the excitation light source that passes until at each point in the volume under observation a temperature is set that deviates by maximum 3° C. from the temperature before the effect.

The switch-off time point $t_{off}$ of the excitation light source is defined as the point in time, at which the excitation intensity I in the volume under observation has decreased to less than 5% of the maximum excitation intensity (e.g. after the pulse of a laser).

Determination of the heating and cooling time: The evolution of the temperature over time at a distance r from the centre of a nanoparticle having radius rNP is obtained by numerically solving the heat conduction equation in a sufficiently large water sphere having radius rMax around the nanoparticle, wherein the nanoparticle itself is removed from the simulation area. By utilizing spherical symmetry, a one-dimensional radial heat conduction equation is obtained, in the area rNP to rMax, t>0:

$$\frac{\alpha}{r^2} \partial_r (r^2 \cdot \partial_r T(r, t)) = \partial_t T(r, t),$$

wherein T(r,t) is the temperature at the position r at the time t and α is the thermal diffusivity of the water ($\alpha = 1.43 \cdot 10^{-7}$ m²/s).

As a starting condition the temperature of the surrounding medium is set before optical excitation to $T_0$: $T(r, 0) = T_0$.

The boundary conditions at the positions rNP and rMax are set as follows: At the position r=rNP the increase of the temperature progression at the point in time t is obtained from the absorbed power of the nanoparticle at the point in time t (Neumann boundary condition):

$$\partial_r T(rNP,t) = P(t)/(4 \cdot \pi \cdot rNP^2 \cdot k)$$

wherein P(t) is the power absorbed by the nanoparticle and k is the thermal conductivity of water (k=0.6 W/(m·K)). The absorbed power is calculated from P(t)=I(t)·σ, with I(t) corresponding to the time-dependent excitation intensity of the light source and σ the absorption cross-section of the part a (i.e. provided that the focus size is not changed, I(t) for example for a CW laser would be a constant, and I(t) would reproduce the time-dependent pulse form for a pulsed laser).

At the position rMax the temperature is kept constant (T(rMax,t)=$T_0$ (Dirichlet boundary condition). For rNP<100 nm, for example rMax 10,000 nm is selected. The thermal diffusivity and thermal conductivity of the water is assumed as a constant. In general, α=k/(C·ρ) applies, wherein C is the specific heat capacity and ρ is the density of water.

By means of suitable programs for the numerical solution of such partial differential equations (e.g. with the command NSolve in mathematics, etc.) the above heat conduction equation can be solved and values obtained for the temperature as a function of the location and the time T(r,t).

For example, for a spherical gold nanoparticle with rNP=30 nm, which is excited with a constant intensity of 1 kW/mm² with 532 nm wavelength for a duration of 100 ns, the following values are obtained for a starting temperature of $T_0$=30° C.: T(r=30 nm, t=20 ns)=70° C., T(r=30 nm, t=100 ns)=78° C., T(r=30 nm, t=120 ns)=36° C., T(r=40 nm, t=20 ns)=56° C., T(r=40 nm, t=100 ns)=64° C., T(r=40 nm, t=120 ns)=36° C.

To determine the heating time according to the invention T(r,t) is evaluated for different times. The heating time is then the shortest time $t_{auf}$, for which the following applies:

$$|T(r;t_{auf})-T(r;2 \cdot t_{auf})| \leq 3° \text{ C. with } r \in [rNP; rMAX]$$

i.e. the amount of the difference of the temperature distribution for the times $t_{auf}$ and $2t_{auf}$ must be less than 3° C. for all points outside of the nanoparticle.

The cooling time is obtained as a difference $t_x - t_{off}$, wherein $t_x$ is the shortest time, for which the following applies:

$$|T(r;t_x)-T_0| \leq 3° \text{ C. with } r \in [rNP; rMAX] \text{ and } t_x > t_{off}$$

The heating time preferably in at least one of the passages of the cycle—in a preferred embodiment of the invention in at least 10, particularly preferably in at least 20, particularly preferably in at least 40, particularly preferably in at least 80, particularly preferably in at least 160 passages of the cycle—is preferably more than 1 nanosecond, particularly preferably more than 5 nanoseconds, particularly preferably more than 10 nanoseconds and preferably less than 100 milliseconds, particularly preferably less than 10 milliseconds, particularly preferably less than 1 millisecond, particularly, preferably less than 300 microseconds, particularly preferably less than 100 microseconds, particularly preferably less than 50 microseconds, particularly preferably less than 30 microseconds, particularly preferably less than 10 microseconds, particularly preferably less than 5 microseconds, particularly preferably less than 1.5 microseconds. Through a short heating time, a short total duration of the method can be achieved.

The cooling time preferably in at least one of the passages of the cycle—in a preferred embodiment of the invention in at least 10, particularly preferably in at least 20, particularly preferably in at least 40, particularly preferably in at least 80, particularly preferably in at least 160 passages of the cycle, is preferably more than 1 nanosecond, particularly preferably more than 5 nanoseconds, particularly preferably more than 10 nanoseconds and preferably less than 100 milliseconds, particularly preferably less than 10 milliseconds, particularly preferably less than 1 millisecond, particularly preferably less than 300 microseconds, particularly preferably less than 100 microseconds, particularly preferably less than 50 microseconds, particularly preferably less than 30 microseconds, particularly preferably less than 10 microseconds, particularly preferably less than 5 microseconds, particularly preferably less than 3 microseconds, particularly preferably less than 1.5 microseconds, particularly preferably less than 1 microsecond, particularly preferably less than 300 nanoseconds, particularly preferably less than 100 nanoseconds. A short cooling time can contribute to an accelerated PCR.

If, through excitation of a nanoparticle, heat is transferred to its environment, this means that energy is transferred to the nanoparticle, wherein the nanoparticle heats its environment through the transfer of the energy. Through the excitation of the nanoparticles, the direct environment of the nanoparticles is preferably heated more than the more distant environment of the nanoparticles. Usually the nanoparticles are initially heated by excitation and then transfer heat to their environment. The environment of the nanoparticles is preferably a spherical volume which has 100 times (100×) the diameter of the nanoparticle located at its centre point, particularly preferably 10× the diameter, more particularly preferably 4× the diameter and preferably less than 2× the diameter.

Through the excitation of the nanoparticles the environment of the nanoparticles is preferably locally heated. Particularly rapid temperature changes are possible if the heated volume only accounts for a small fraction of the total volume. On the one hand, with just a small energy input through irradiation, a high temperature difference can already be produced. On the other hand, a very rapid cooling of the heated volume is possible if a sufficiently large cold temperature tank is present in the irradiated volume in order to cool the nanoparticles and their environment again after the irradiation. This can be achieved by the nanoparticles being irradiated sufficiently greatly (in order to reach the desired temperature increase) and sufficiently shortly (in order that the heat remains localized). It is possible through local heating to expose the polymerases to a lower heat, so that PCR methods with a number of cycles exceeding 80 can also be realised.

A local heating in the sense of the present invention is present if the duration of the excitation in the respectively irradiated volume (e.g. in the laser focus) t is selected to be shorter than or equal to a critical excitation duration t1. The excitation duration t1 is hereby preferably equal to the duration of effect $t_A$. t1 is hereby determined by the time required by the heat to diffuse, with an average nanoparticle distance, from one nanoparticle to the next, multiplied by a scaling factor s1. In the case of an average nanoparticle distance |x| and a temperature conductivity D of the medium between the nanoparticles, t1 is given by:

$$t1 = (s1 \cdot |x|)^2 D,$$

wherein the temperature conductivity D typically in an aqueous solution has a value of $D=10^{-7}$ m²/s.

The scaling factor s1 is a measure of how far the heat front of a particle spreads during the excitation duration. The temperature increase through an excited nanoparticle at a distance of a few nanoparticle diameters is only a very small fraction of the maximum temperature increase on the particle surface. In one embodiment of the invention an overlap of the heat fronts of a few nanoparticles is allowed in the sense that, in order to define the critical excitation duration t1 using the abovementioned formula, a scaling factor s1 of greater than 1 is used. In another embodiment of the invention, no overlap of the heat fronts is allowed during the excitation duration (corresponding to a greatly localized heating) in the sense that, in order to define the critical excitation duration t1 using the abovementioned formula, a scaling factor s1 of less than or equal to 1 is used. To define the local heating, preferably s1=100, preferably s1=30, preferably s1=10, preferably s1=7, preferably s1=3 and more particularly preferably s1=1, preferably s1=0.7, preferably s1=0.3.

Values for s1>1 can be advantageous, inter alia, for example in such cases in which the irradiated volume has a high aspect ratio (for example in the focus of a moderately focused laser beam), so that there is a comparably high number of nanoparticles located at the surface of the irradiated volume, and fewer heated nanoparticles are therefore located in their environment, and a significant heat removal from the irradiated volume takes place, so that the heating contribution of the more remote neighbours remains negligible for longer.

This means that, for example in the case of a nanoparticle concentration of 1 nM, which results in an average nanoparticle distance of |x|=1.2 micrometres, local heating is present, insofar as the excitation duration is less than t1=14 microseconds (the scaling factor is selected here as s1=1, $D=10^{-7}$ m$^2$/s). It is to be assumed that if t>t1 is selected, the heat emitted by the nanoparticles can consequently cover, through diffusion, during the irradiation, a distance that is greater than the average nanoparticle distance and this leads as a result to a superimposition of the heat fronts of many nanoparticles so that a temperature increase takes place in the whole volume between the nanoparticles. The temperature increase should be spatially more homogeneous in the irradiated volume, the longer it is heated, as not only the contributions of the closest nanoparticles but also of more remote neighbours are included in the temperature distribution around a nanoparticle. If the reaction volume is irradiated with a radiation absorbed by the nanoparticles for longer than t1, the heating is described as global.

A global heating can also take place, e.g., in that the reaction volume is heated from externally with a Peltier element or a resistance heater. The global heating can also be carried out in that, e.g. the reaction volume is irradiated with a radiation that is absorbed by the water in the sample more greatly than, or similarly greatly to, its absorption by the nanoparticles. "Temperature increase" hereby means the difference between the temperature at a location at the observation time directly after the excitation and the temperature at the same location at the time directly before the excitation. Global heating and local heating can also be carried out simultaneously.

Through the excitation of nanoparticles it can be achieved that in the PCR method of nucleic acids, it is not the whole reaction volume that must be heated. On the other hand it is possible to heat only specific parts of the reaction volume through excitation of nanoparticles. It is advantageously possible to heat only the parts of the reaction volume that must be heated for the amplification of the nucleic acids. In this way, heat-sensitive constituent parts of the sample can be protected, such that a higher number of cycles is facilitated. Local heating can be more rapid than global heating of the whole reaction volume if less energy needs to be transferred. Therefore, it is advantageously possible through the invention to provide a PCR method which is quicker and requires less energy.

The excitation of the nanoparticles preferably takes place through an alternating field, particularly preferably through an electromagnetic alternating field, more particularly preferably optically. The excitation preferably takes place with light in the range from far infrared to far ultraviolet (in a range of from 100 nm to 30 μm wavelength), particularly preferably in the range of from near infrared to near ultraviolet (in a range of from 200 nm to 3 μm wavelength), more particularly preferably through visible light (in a range of from 400 nm to 800 nm wavelength). This can offer the advantage, with respect to the conventional global heating of the reaction vessel from externally, that the thermally insulating wall of the reaction vessel does not need to be overcome, as the energy is transferred directly to the nanoparticles. A quicker heating of the desired portion of the sample is thus achieved.

The light particularly preferably has a frequency that excites the surface plasmon resonance of the nanoparticles. The light source can provide the light pulsed or continuously. The light can, e.g., be a gas laser, a diode laser or a diode-pumped solid body laser.

The excitation duration, during which the nanoparticles are optically excited in the respectively irradiated volume per cycle, is preferably more than 1 picosecond, particularly preferably more than 30 picoseconds or 100 picoseconds, more particularly preferably longer than 1 nanosecond or 10 nanoseconds. At the same time the duration of effect is preferably less than 100 ms, particularly preferably less than 10 ms, particularly preferably less than 1 ms, particularly preferably less than 500 μs, particularly preferably less than 100 μs, particularly preferably less than 50 μs and more particularly preferably less than 10 μs. If the excitation serves for denaturing, the excitation duration preferably corresponds to the duration of effect $t_A$.

The excitation duration is preferably shorter than it takes on average until the heat arising in the environment of the nanoparticles diffuses through the average particle distance, so that on average no significant overlap of the heat fronts of neighbouring particles takes place. The time interval of the excitation is particularly preferably selected so that the temperature increase, produced by the irradiation, around each irradiated nanoparticle on average at a distance of 20 nanoparticle diameters, particularly preferably 2 nanoparticle diameters, more particularly preferably 1 nanoparticle diameter, falls to less than half of its maximum. In one embodiment, an irradiation duration that is as short as possible per volume unit is preferred so that a de-hybridized DNA single strand can diffuse away from the nanoparticle, during the denaturing, only less than 100 nm, particularly preferably less than 20 nm, particularly preferably less than 10 nm, particularly preferably less than 5 nm. There is thereby a high probability that the de-hybridized DNA single strand will bind to an oligonucleotide on the same nanoparticle ("re-hybridization"). This can facilitate an accelerated method. In one preferred embodiment the concentration of the nanoparticles conjugated to primers is less than 10 nM. The time interval of the excitation is thereby particularly preferably between 1 ns and 10 μs, particularly preferably between 10 ns and 1 μs and more particularly preferably between 15 ns and 300 ns. The time interval of the excitation is preferably selected to be not substantially shorter than 1 ns, as otherwise the time of heating of the DNA double strand is not sufficient for the two contained single strands to be able to sufficiently separate from each other through diffusion so that they do not immediately hybridize with each other again. If the time interval of the excitation serves for the denaturing, it preferably corresponds to $t_A$.

The duty factor is the ratio of the duration of effect to the duration of a PCR cycle $t_c$. The duty factor is preferably selected to be so great that the excitation leads to a sufficient denaturing of the DNA double strands through local heating. At the same time the duty factor is preferably selected so that the average temperature increase of the whole sample is kept sufficiently small so that no interfering influences on hybridization, elongation and denaturing arise. The duty factor for the irradiated volume is preferably less than 50%, particularly preferably less than 20% and more particularly preferably less than 1%. The duty factor in the irradiated volume is suitably more than $10^{-12}$, preferably more than $10^{-10}$, particularly preferably more than $10^{-9}$ and more particularly preferably more than $10^{-8}$.

In the sense of the present invention the power density is the optical power per area unit of the light impinging into the sample. If it is a pulsed light source the peak power is relevant. The power density, with which the nanoparticles are excited, is, preferably in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, more than 10 W/mm$^2$, particularly preferably more than 50 W/mm$^2$, particularly preferably more than 100 W/mm$^2$, particularly preferably more than 200 W/mm$^2$, particularly preferably more than 300 W/mm$^2$ and more particularly preferably more than 400 W/mm$^2$. With this embodiment of the invention it can be advantageously achieved that the nanoparticles are sufficiently heated through the excitation.

The power density, with which the nanoparticles are excited, is preferably in at least one passage of the cycle, particularly preferably in at least 10 passages of the cycle, particularly preferably in at least 20 passages of the cycle, particularly preferably in at least 40 passages of the cycle, particularly preferably in at least 80 passages of the cycle and more particularly preferably in at least 160 passages of the cycle, less than 20,000 kW/mm$^2$, preferably less than 10,000 kW/mm$^2$, particularly preferably less than 5000 kW/mm$^2$, particularly preferably less than 3000 kW/mm$^2$, particularly preferably less than 1000 kW/mm$^2$, particularly preferably less than 500 kW/mm$^2$, particularly preferably less than 300 kW/mm$^2$, particularly preferably less than 150 kW/mm$^2$ and more particularly preferably less than 80 kW/mm$^2$. With this embodiment of the invention, damage to the nanoparticles or the DNA bound thereto can advantageously be counteracted or prevented.

In a further preferred embodiment the energy of the excitation radiation is transferred through the material absorption of the nanoparticles to these nanoparticles. The light used to excite the nanoparticles can also come e.g. from a thermal radiator, e.g. a flashing light. In a further preferred embodiment of the invention the nanoparticles are excited through an electromagnetic alternating field or electromagnetic waves that generate eddy currents in the nanoparticles. With a suitable form of the nanoparticles it is also possible to excite the nanoparticles with ultrasound.

In a preferred embodiment of the invention the nanoparticles are conjugated to oligonucleotides. The nanoparticles form in this way nanoparticle-oligonucleotide conjugates. It can therefore advantageously be achieved that oligonucleotides that are parts of the method according to the invention are specifically heated through excitation of the nanoparticles without the whole reaction volume having to be heated. In a particularly preferred embodiment the nanoparticles are conjugated to primers. More particularly preferably the nanoparticles are conjugated to the forward and reverse primers of the PCR method. In a preferred embodiment of the invention, forward primers, but no reverse primers, are attached to one class of nanoparticle-oligonucleotide conjugates, and reverse primers, but no forward primers, are attached to a different class.

In a further preferred embodiment a class of conjugates of nanoparticles and oligonucleotides is conjugated both with forward and also reverse primers. In this embodiment, in the PCR method, starting from the forward primer on a nanoparticle, a new DNA single strand complementary to the original is written. This new DNA single strand is conjugated to the nanoparticle, as the new DNA single strand contains the forward primer. Directly after writing, the new DNA single strand forms, with the original, a double strand.

In a subsequent denaturing step the new DNA single strand is separated from the original. At an annealing temperature the new DNA single strand hybridizes with a reverse primer, which is located on the surface of the nanoparticle, so that a loop is produced. For hybridization with the reverse primer of the same nanoparticle, only a short distance must be covered. For hybridization with a reverse primer on a different nanoparticle, a longer distance must be covered on average with preferred concentrations of nanoparticles. It can thus be advantageously achieved in this embodiment that the annealing takes place more quickly and the PCR method can be performed more quickly.

In a preferred embodiment of the invention the nanoparticles are combined with the oligonucleotides such that covalent bonds with more than one thiol are present between oligonucleotides and nanoparticles. PCR buffers generally contain dithiothreitol, which destabilizes the thiol bond between a gold nanoparticle and an oligonucleotide and which can lead, in particular with thermal loading such as e.g. during the denaturing, to oligonucleotides detaching from the nanoparticles. Covalent bonds with more than one thiol between primers and nanoparticles can reduce the detachment of the primers and thus increase the efficiency of the PCR method.

In a preferred embodiment, counter-sequences are used, which can combine with such oligonucleotides that have detached from the nanoparticles, with which they were previously combined. Counter-sequences are oligonucleotides. It can arise in the method that oligonucleotides conjugated with nanoparticles detach from these and thus become free. If these free oligonucleotides are the primers according to the invention, these free primers can bind to the original or complement. Since, however, the free primers are not bound to nanoparticles, the free primers cannot be de-hybridized, through excitation of the nanoparticles, from the original or complement. The efficiency and sensitivity of the method thereby fall. The counter-sequences are at least partially complementary to the free oligonucleotides and bind to them with sufficient affinity, so that the function of the free oligonucleotides is limited. The efficiency and sensitivity of the method can thereby be increased. In a particularly preferred embodiment of the method, already before the addition of the original to the sample, counter-sequences are given to the sample in a sufficient amount in order to block the free primers. At the same time the amount is small enough so that a sufficiently high number of unblocked primers are still located on the nanoparticles. This is possible if the number of primers on the nanoparticles exceeds the number of free primers.

In a preferred embodiment of the invention, filling molecules are applied to the nanoparticles. The filling molecules prevent the undesired aggregation of the nanoparticles in the sample. The filling molecules thus advantageously serve to stabilize the nanoparticles. The charge of the nanoparticles can be modulated through the filling molecules. It is hereby possible to adapt the salt concentration found in the environment of the nanoparticles so that the DNA polymerase can synthesize as quickly as possible and the method can be performed advantageously quickly. The filling molecules can consist of oligonucleotides, but which are not primers and are preferably shorter than the primers. The filling molecules can also consist, e.g., of polymers, such as e.g. polyethylene glycol. In a preferred embodiment, the filling molecules allow the number of primers on the nanoparticles to be reduced, and instead to use more filling sequences, without causing significant losses in the efficiency of the method.

In a further preferred embodiment of the method, the oligonucleotides have a spacer sequence as a sub-sequence on the nanoparticles. The spacer sequence thereby lies on the side of the respective oligonucleotide facing towards the nanoparticle. The spacer sequence thus serves as a spacer for the rest of the oligonucleotides. In a preferred embodiment an oligonucleotide contains both a sub-sequence that has the function of a primer and is described as a primer sequence, and also a sub-sequence that is a spacer sequence. Due to the fact that the primer sequences are spaced further apart from the nanoparticles through the spacer sequences, the nucleic acids to be amplified and the DNA polymerases can advantageously have better access to the primer sequences. In a preferred embodiment, after being synthesized, the copies of the original and of the complement remain, via the spacer sequences, fixed on the surface of the nanoparticles. In a particularly preferred embodiment the spacer sequences have detection sequences of restriction endonucleases, so that the synthesized copies can be separated off from the nanoparticles. This is preferably realised after the end of the method, but can also arise during the method. It is possible with the method to produce copies of nucleic acids, which are present freely in the sample. In a preferred embodiment of the method, the spacer sequences are at least just as long as the filling molecules, so that the primer sequences are not covered by the filling molecules.

In a preferred embodiment the heat transferred through the excitation of the nanoparticles to their environment is sufficient in order to de-hybridize the oligonucleotides on the surface of the nanoparticles from nucleic acids hybridized with the oligonucleotides. In this embodiment nanoparticles are conjugated to oligonucleotides and at least some of these oligonucleotides are hybridized with at least partially complementary nucleic acids. Through the excitation of the nanoparticles, thermal energy is transferred to the surrounding water so that the temperature of the water around the nanoparticles preferably suffices in order to denature the oligonucleotides from the nucleic acids combined with them. In a particularly preferred embodiment, the nanoparticles are conjugated to primers. When performing the PCR method, preferably double-stranded PCR products are thereby produced, wherein in each case at least one single strand of the double-stranded PCR products is conjugated to a nanoparticle. Through excitation of the nanoparticles it can advantageously be achieved in this embodiment to produce the denaturing temperature around the nanoparticles and to perform the denaturing of the double-stranded PCR products without the whole reaction volume having to be heated. The denaturing can thereby be accelerated and the PCR method thus takes place more quickly. In a further preferred embodiment, the annealing temperature and the elongation temperature are also produced through the excitation of the nanoparticles. In comparison with heating the whole sample to the annealing and elongation temperature, it is preferably only necessary to transfer a small amount of energy. Denaturing, annealing and elongation of the PCR method take place particularly preferably without global heating, but instead exclusively via local heating through excitation of the nanoparticles. In this way the method can be carried out without a means for global heating, so that less apparatus is required to carry out the method.

In a further preferred embodiment the method includes a global heating step. The temperature of at least one method step is reached at least partially through global heating. In a particularly preferred embodiment the annealing temperature is reached by global heating of the reaction volume. More particularly preferably, the reaction volume is maintained in a predetermined temperature range, in which the annealing takes place, throughout the whole method and beyond by global heating. The elongation temperature and the denaturing temperature are thereby reached through excitation of the nanoparticles. The means that generates the global heating can advantageously be kept very simple in its construction, as it must only maintain one predetermined temperature.

In a further preferred embodiment the annealing temperature and the elongation temperature are reached by global heating and exclusively the denaturing is produced through excitation of the nanoparticles. It can advantageously be achieved that the means that brings about the global heating has to produce a temperature cycle with only two different temperatures and can therefore be kept constructively simple. The elongation and the annealing usually take place in each case in a narrow temperature range. On the other hand, only one certain temperature must be surpassed for denaturing. Therefore, non-homogeneities in the excitation of the nanoparticles can be less of a problem for the production of the denaturing than when setting the annealing and elongation temperature. Consequently a preferred embodiment, in which the excitation of the nanoparticles serves exclusively for denaturing, can be realized technically more simply. In particular this applies to the particularly preferred case, in which the annealing temperature and the elongation temperature are very close to each other, e.g. with an annealing temperature of 60° C. and an elongation temperature of 72° C., so that global heating must only produce a small temperature increase.

In a particularly preferred embodiment the annealing temperature is equal to the elongation temperature. If the annealing temperature is equal to the elongation temperature, only one temperature cycle with two different temperatures is usually necessary to perform the PCR method, whereby the method can be carried out in a simple structure. The melt temperatures of the primers and the DNA polymerase used are particularly preferably selected so that at the melt temperature the DNA polymerase used can still synthesize DNA at a sufficient speed. In a particularly preferred embodiment the elongation temperature, which is equal to the annealing temperature, is reached by global heating and the denaturing is achieved through excitation of the nanoparticles. In this way the means that brings about the global heating can have a simpler constructive design, as it only has to maintain one temperature.

In one preferred embodiment, the excitation of only a portion of the nanoparticles takes place at each point in time of the method. For this, e.g. the means serving for exciting the nanoparticles can be designed so that it excites the nanoparticles present only in a part of the reaction volume. In a particularly preferred embodiment the nanoparticles are optically excited and the optics system that guides the light of the light source into the reaction volume is designed so that light is guided only into one part of the reaction volume. The portion of the nanoparticles that is excited preferably changes in the course of the method. In other words, a first amount of nanoparticles, which are excited at a first time point, is not identical to a second amount of nanoparticles, which are excited at a second time point. In this case any desired number of nanoparticles can be present in the first amount and any desired number of nanoparticles present in the second amount, provided that the first and second amounts are not identical. One of the two aforementioned amounts may, e.g., partially coincide with the other so that the two amounts form an intersection. One of the amounts can, e.g., be a sub-amount of the other amount, so that one amount contains fewer nanoparticles than the other amount. The two amounts can e.g. also be designed so that they do not form an intersection and therefore no nanoparticle is simultaneously present both in the first amount and in the second amount. One of the two amounts can also be the empty amount (zero), so that e.g. nanoparticles are excited at one time point and no nanoparticles are excited at another time point. In a preferred embodiment the first and the second amounts contain substantially the same number of nanoparticles. A light source particularly preferably excites different portions of the nanoparticles at different times. In the embodiment of the method a light source can thereby be used with a lower power which just suffices to excite a portion of the nanoparticles. In a particularly preferred embodiment, two or more light sources are used to excite different portions of the nanoparticles. It is advantageously possible to excite different portions of the nanoparticles without an optical element being required that guides the light source onto different parts of the reaction volume.

In a further preferred embodiment of the invention a directed movement of the sample relative to an excitation field takes place so that nanoparticles in different sub-volumes of the sample are excited at different times. The excitation field is particularly preferably the light of a laser. In a more particularly preferred embodiment the light of the light source is guided by an optical element so that nanoparticles in different sub-volumes of the reaction volume are excited with the light at different times. The optical element can be arranged to be movable, e.g. the optical element can contain a movable mirror, a spatial modulator or an acousto-optic modulator. The light source itself can also be arranged to be movable. The movement of the sample can also be realized so that the reaction vessel containing the sample is moved. In a particularly preferred embodiment both the light beam and also the reaction vessel are moved. In a further preferred embodiment the sample is moved in the reaction volume, so that the light of the light source detects different sub-volumes of the sample at different times. This can be achieved e.g. by the sample being stirred in the reaction volume, e.g. by a magnetic stirrer. The reaction volume can e.g. be in an elongated form, e.g. a duct or a tube. The sample can e.g. be moved through a duct, wherein the sample passes through a light beam at one or more positions. A sample particularly preferably flows through a duct and passes n positions, at each of which a light beam is directed onto the sample in the duct, wherein through the linear flow of the sample through the n light beams a PCR method with n cycles is carried out. n is thereby preferably greater than 80. The method can be advantageously carried out with a small number of movable parts. By using a duct, a minia-turisation, e.g. in the sense of a lab-on-chip, is also possible. The denaturing is preferably produced through the light beam, while the elongation and annealing temperature are produced by global heating. The elongation temperature is particularly preferably equal to the annealing temperature so that only one temperature has to be maintained by global heating. In this way the method according to the invention can advantageously be carried out with a low level of resources.

In a preferred embodiment a DNA polymerase that is thermolabile is used in the method. If the excitation of the nanoparticles is used for denaturing it is possible to avoid the whole reaction volume being exposed to high temperatures. It is instead possible to bring only the direct environment of the nanoparticles to the denaturing temperature. The DNA polymerases that are not located in this direct environment are not therefore exposed to high temperatures. It is thereby possible to also use DNA polymerases that are not heat-stable, thus thermolabile. Through the inclusion of the thermolabile DNA polymerases, therefore, a larger selection of DNA polymerases is available for the method according to the invention. Through the greater selection of DNA polymerases the reaction conditions can be changed to a greater extent and at the same time a sufficient functioning of the respective DNA polymerase can be maintained. In order that the nucleic acids to be amplified can bind to the negatively charged oligonucleotides on the nanoparticles, it may be necessary to use substances—in particular salts—in the sample in concentrations that negatively influence the functioning of a thermostable DNA polymerase, which reduces the efficiency of the method. The greater selection of DNA polymerases—in particular those having a high toler-ance for salts—can lead to an increase in the efficiency of the method being achieved. Part of the larger selection of DNA polymerases are small DNA polymerases such as e.g. the Klenow fragment and Phi29. In the proximity of the nano-particles, large thermostable DNA polymerases can experi-ence a steric hindrance through the applied and possibly already elongated primers. It can thereby arise that the DNA polymerase does not arrive at the nucleic acid to be copied, or the DNA polymerase breaks off before it has synthesized a complete copy of the original or complement, which signifies a reduction in the efficiency of the method. The greater selection of DNA polymerases thus facilitates an increase in the efficiency of the method. Through the larger selection of DNA polymerases, enzymes with lower pro-duction costs are also advantageously available. The DNA polymerases that are not located in the direct environment of the nanoparticles experience a lower heat-related deactiva-tion. It is thereby advantageously possible to use a smaller amount of DNA polymerase in the method.

In a preferred embodiment of the invention, both soluble primers and also primers on nanoparticles are present in the reaction volume. The soluble primers are not conjugated to nanoparticles, but instead are dissolved in the sample. The soluble primers have preferably smaller dimensions than the nanoparticle-primer conjugates and can be present in a higher concentration than the nanoparticle-primer conju-gates. Therefore, the soluble primers can have better and quicker access to long, double-stranded nucleic acids such as e.g. genomic DNA. In a particularly preferred embodi-ment, in a first step of the method the long, double-stranded nucleic acids are denatured by global heating of the whole reaction volume, after which the dissolved primers hybridize with the nucleic acids. The PCR method thereby initially takes place in one or more cycles with global heating, the DNA polymerase thereby synthesizes the desired, short copies of the long, double-stranded nucleic acids. After this, the PCR method is continued, wherein local heating is also used through excitation of the nanoparticles.

In a preferred embodiment of the invention the particle diffusion of the nanoparticle-primer conjugates can be rein-forced by optical fields. By means of optic eddy fields (according to Silvia Albaladejo et al., Nano Letters, 2009, Volume 9, Issue 10, pages 3527 to 3531, of which the related content is part of the present disclosure through reference thereto), with which the nanoparticles are excited, or through optic forces (according to Arthur Ashkin et al., Proc. Natl. Acad. Sci., 1997, Volume 94, Issue 10, pages 4853 to 4860, of which the related content is part of the present disclosure through reference thereto), which can be exerted on the nanoparticles, the nanoparticle diffusion can be increased. It can advantageously be achieved that, with a given nanoparticle concentration, a more rapid hybridization of the nucleic acids to be amplified takes place with the primers on the nanoparticles. This can be used to accelerate the method according to the invention.

In one embodiment of the invention the concentration of the products of the amplification reaction is determined by test probes. Test probes are nanoparticles which have, on their surface, oligonucleotides with test sequences. In a preferred embodiment of the method the oligonucleotides of the test probes have a spacer sequence as a sub-sequence. The spacer sequence is thereby on the side, facing towards the nanoparticle, of the respective oligonucleotide. The spacer sequence thus serves as a spacer for the rest of the oligonucleotide. In a preferred embodiment an oligonucleotide of the test probes contains both a sub-sequence that is described as a test sequence and also a sub-sequence that is a spacer sequence. In a preferred embodiment, filling molecules are applied to the test probes. The test sequences can hybridize with products of the amplification reaction. The test sequences are thereby preferably at least partially complementary to the products of the amplification reaction. In a preferred embodiment first nanoparticles are conjugated to forward primers. In the presence of the original and a DNA polymerase the forward primers are extended so that complements are produced, which are bound via the forward primers to the first nanoparticles. A complement consists of the forward primer and an extension sequence, which arises through the extension of the forward primer. Particularly preferably, using free and/or nanoparticle-bound reverse primers, a PCR method is carried out so that in an exponential amplification a large number of copies of the original and nanoparticle-bound complements are preferably produced. More particularly preferably, the first nanoparticles have, on their surface, both forward primers and also reverse primers. In an optional intermediate step, the originals and possibly copies thereof are denatured from the complements through local or global heating. The first nanoparticles are then brought together with test probes if this has not already taken place. The test sequences of the test probes are complementary to the extension sequences, such that the test probes can bind via test sequences to the extended forward primers on the first nanoparticles. Under suitable reaction conditions the combination of the first nanoparticles with the test probes comes about to the same extent as that in which nanoparticle-bound complements are also present. This means that, if no extension sequences are produced, no combination of test probes and first nanoparticles arises.

The reaction conditions of the amplification according to the invention and the detection through test probes are particularly preferably selected so that the degree of combination of first nanoparticles with test probes allows conclusions to be drawn concerning the concentration of the original that was present in the sample before the amplification. Through the combination of the first nanoparticles with the test probes a measureable change can arise, e.g. a redshift or broadening of the plasmon resonance in the extinction spectrum. In a more particularly preferred embodiment the measurable change that arises through the combination of test probes and first nanoparticles is proportional to the concentration of the original in the sample before the amplification. Concentration detection can thus advantageously be realized with simple means.

In a further preferred embodiment the method includes forward primers, which are conjugated to first nanoparticles, and free and/or nanoparticle-bound reverse primers. It is particularly preferred that the first nanoparticles have both forward primers and also reverse primers on their surface. In a first step, the forward primers are extended in the presence of the original through a DNA polymerase to nanoparticle-bound complements. In a second step, starting from the reverse primers, which bind to the nanoparticle-bound complement, copies of the original are synthesized. Subsequently the first nanoparticles are brought together with test probes if this has not already taken place. The test sequences in this embodiment are complementary to the forward primers. If the forward primers have not been extended, the test probes can bind well to the first nanoparticles. If the forward primers have been extended, the binding of test sequences to forward primers is hindered by steric hindrance. If a newly synthesized copy of the original is hybridized with the extended forward primer, the binding of the test sequence to the extended forward primer is prevented. In this way, the degree of combination between first nanoparticles and test probes decreases to the same extent as that in which products of the amplification reaction, i.e. complements and copies of the original, were synthesized. With a suitable selection of the reaction conditions a concentration detection of the original in the sample can be carried out, so that a measurable change is smaller, the more original that was present in the sample before the amplification. The measurable change can thereby be, e.g., a redshift or broadening of the plasmon resonance in the extinction spectrum. A simple test can advantageously be designed which allows the determination of concentrations of specific nucleic acids.

Through the invention it is possible to provide an improved method for the amplification of nucleic acids.

Figure 1:
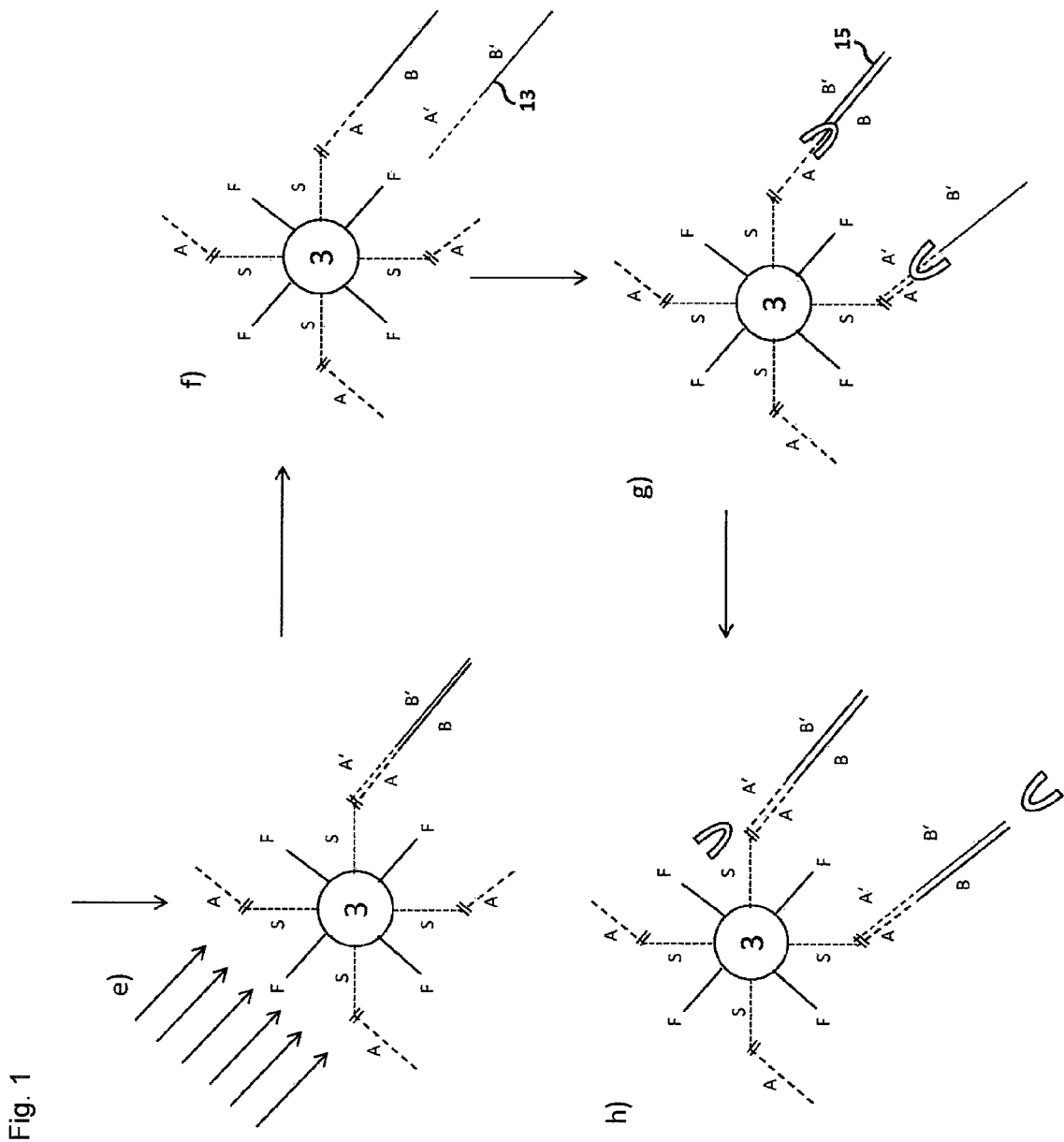
FIG. 1 shows in a schematic illustration nanoparticles that are conjugated with filling molecules, spacer sequences, abasic modifications and primer sequences.

DETAILED DESCRIPTION OF THE INVENTION BY REFERENCE TO A PLURALITY OF EXEMPLARY EMBODIMENTS

In known PCR methods for the amplification of a short nucleic acid (e.g. with fewer than 300 base pairs), which work with tempering by means of thermocyclers, the process duration is generally limited by the tempering time, which accounts for a large part of the cycle duration. In order to achieve a process duration that is as short as possible, it is endeavoured in such cases, with respect to the yield $g_h$ (the index "h" points towards this conventional case) per passage of the cycle, to arrive close to the theoretical threshold of 100%, in order to achieve the desired result with as few cycles as possible. According to the findings of the inventors, however, in methods with shorter tempering times, e.g. in methods that work with local heating by means of nanoparticles, a maximization of the yield g is no longer necessarily the best strategy. Instead, here, taking into account a reduced yield, a shortening of the cycle duration that outweighs the disadvantages of the lower yield can be achieved, such that overall, despite lower yield, shortening of the process duration results.

Without adhering to a certain theory, it is firstly necessary to observe the characteristic time constants required by different processes during the PCR and a simple mathematical model is to be formulated.

Firstly, a conventional PCR method is assumed, which is carried out in a customary thermocycler, e.g. with a Peltier element or an air stream in order to temper the reaction volume (usually 5 to 50 microlitres) from externally. Such customary thermocyclers typically achieve heating and cooling rates of approximately 5 K/s, even if the average tempering speed may be significantly lower. This means that the process of heating a sample from an annealing temperature of 60° C. to a denaturing temperature of 95° C. and then cooling it again to the annealing temperature can require at least approximately:

$$2 \cdot 35°C. / \left(5 \frac{°C.}{s}\right) = 14 \ s.$$

Added to this is the fact that, with methods used thus far, the thermalization of the sample volume can additionally take a few seconds until approximately the same temperature prevails everywhere in the sample, such as on the heated or cooled vessel walls. Consequently, the total tempering time $t_t$ per cycle in conventional protocols is typically more than 14 s.

For a PCR, the annealing and elongation times are also important. The annealing time in the case of sufficiently high primer concentrations (e.g. more than 300 nM) under suitable conditions in the prior art is frequently a few seconds until a primer is hybridized to the majority (>90%) of the targets. For example an annealing time of 1 s can also be realized.

The time required by the polymerase for elongation of the primers depends upon the length of the amplicon and the write speed of the polymerase used. In order to elongate, for example, 80 base pairs, the elongation under suitable conditions, in the case of a polymerase with effective write speed of 100 BP/s, takes approximately 0.8 s.

The hybridization time and the elongation time together are referred to below as the required productive time $t_{ph}$. In the above example, the required productive time for a short amplicon is for example $t_{ph}$=2 s, if one second is assumed for annealing and a further second for elongation.

The duration of a PCR cycle $t_{ch}$ in the abovementioned example is the sum of the tempering time $t_{th}$ and the required productive time $t_{ph}$, i.e.:

$$t_{ch} = t_{th} + t_{ph} \quad (3)$$

If any dwell time at the denaturing temperature is disregarded, as it can be selected to be very short, e.g. it can be shorter than one second.

If the tempering time of approximately 14 s is compared with the required productive time of approximately 2 s in the above example, it can be seen that, in a conventional thermocycler for short nucleic acids, the following inequalities typically apply: $t_{th} \gg t_{ph}$ and $t_{ch} \approx t_{th}$. This means that the tempering time, i.e. the heating and cooling times, thus the time taken to bring the sample from the annealing temperature to the denaturing temperature and cool it back down steadily to the annealing temperature, generally determines the duration of each cycle and thus also the total duration of the PCR.

If the number of copies $N_0$ of the template is to be increased to $N_k$ copies with the PCR, this can—as already explained above—be achieved with a number k of temperature cycles, wherein $k = \log_{(1+g_h)}(N_k/N_0)$ if the average yield in each cycle is $g_h$. It is assumed once again for simplification purposes that the yield per cycle remains constant during the PCR. If $f_{c0}$ cycles are carried out per time unit (with $f_{ch} = 1/t_{ch}$, the number of the copies $N_k$ after a time t can be given by:

$$N_k = N_0 (1+g_h)^{f_{ch} t} \quad (4)$$

wherein $g_h = 0 \ldots 100\%$. The process duration T of the whole PCR can be given by the cycle duration $t_{ch}$ multiplied by the necessary number of cycles k:

$$T = t_{c_h} \cdot k = t_{c_h} \cdot \log_{(1+g_h)}\left(\frac{N}{N_0}\right). \quad (5)$$

For example, an amplification by the factor $N_k/N_0 = 10^{12}$, depending on the value of $g_h$, can require the times shown in Table 1.

TABLE 1

Preferred PCR durations T in units of the cycle duration $t_{ch}$ to the $10^{12}$ times amplification of a target.

| $g_h$ | T[$t_{ch}$] |
| --- | --- |
| 0.4 | 82 |
| 0.6 | 59 |
| 0.80 | 47 |
| 1.00 | 40 |

It follows from this that in the case of a conventional PCR, wherein $t_{th} \gg t_{ph}$ and $t_{ch} \approx t_t h$, a short process duration can be achieved by the yield per cycle being maximized, $g_h$ thus being close to 100%. In this case, the number of copies $N_k$ with the time can be given by:

$$N_k = N_0 (1+1)^{f_{ch} t} = N_0 \cdot 2^{f_{ch} t}, \quad (6)$$

i.e.: for each cycle, the number of copies thus far can have added to it the same number (i.e. being doubled for each cycle). The shortest possible PCR duration $T_{min}$ for an amplification by the amplification factor $N_k/N_0$ can then be given by:

$$T_{min} = t_c \cdot k = t_c \cdot \log_2\left(\frac{N_k}{N_0}\right). \quad (7)$$

A different situation can emerge if the tempering times no longer determine the cycle duration. This case includes in particular also the sub-case that heating and cooling steps, including the thermalization, are negligibly short, i.e. if the following inequalities apply: $t_t \ll t_p$ and $t_c \approx t_p$.

Example 1

The effect of shortening the cycle duration is to be examined below. The cycle duration in this example is described as $t_{ci}$ (the optional index "i" is used below to emphasize the solution according to the invention for the parameters, which describes a PCR with shortened cycle durations), wherein the example cycle duration $t_{c_i}$ has been shortened, with respect to the cycle duration $t_{c_h}$ in the conventional case, by a shortening factor x with $$x \varepsilon \mathbb{R}^{>1}$$

so that the following applies:

$$t_{c_i} = \frac{t_{c_h}}{x}.$$

i.e.: the new cycle frequency $f_{c_i} = x \cdot f_{c_h}$ can be calculated from the cycle frequency $f_c$ of the conventional case. The yield in this example is described with $g_i$. The example yield can be equal to the yield in the conventional case ($g_i = g_h$), but it can also be smaller than this ($g_i < g_h$). If there is a reduction in the yield per cycle, this can be described by an efficiency loss factor y, wherein:

$$g_i = \frac{g_h}{y}.$$

It follows that in this example:

$$N_i = N_0 \left(1 + \frac{g_h}{y}\right)^{f_{c_h} \cdot x \cdot t} = N_0 (1 - g_i)^{f_{c_i} \cdot t} = N_0 (1 - g_i)^{f_{c_h} \cdot x \cdot t}. \quad (8)$$

The process duration $T_i$ of the whole PCR in this example is therefore:

$$T_i = \frac{t_{c_h}}{x} \cdot \log_{(1+g_i)}\left(\frac{N_i}{N_0}\right), \quad (9)$$

for which the fact that preferably $$f_{c_h} = \frac{1}{t_{c_h}}.$$

has one again been utilized.

A shortening of the process duration in comparison with the conventional case can be achieved both if $g_i = g_h$ and also if $g_i < g_h$, provided that the disadvantage of the lower yield is outweighed by the advantage of shortening of the cycle duration.

If for example amplification by the factor $N_1/N_0 = 10^{12}$ is assumed, according to Equation (9) the following values can be given for the process duration in units of $t_{c_h}$ as a function of the selection of the values for $g_i$ and x.

TABLE 2

PCR durations T of a conventional PCR and preferred PCR durations $T_i$ in units of the conventional cycle duration $t_{c_h}$ to $10^{12}$ times amplification of a target.

| | | Conventional PCR duration | x | | | | | | |
|---|---|---|---|---|---|---|---|---|---|
| | | T with x = 1 | 1.11 | 1.25 | 1.33 | 1.67 | 2.00 | 4.00 | 10.00 |
| $g_i$ | 0.05 | 566 * | 510 * | 453 * | 425 * | 340 * | 283 * | 142 * | 57 * |
| | 0.10 | 290 * | 261 * | 232 * | 217 * | 174 * | 145 * | 72 * | 29 |
| | 0.15 | 198 * | 178 * | 158 * | 148 * | 119 * | 99 * | 49 * | 20 |
| | 0.20 | 152 * | 136 * | 121 * | 114 * | 91 * | 76 * | 38+ | 15 |
| | 0.25 | 124 * | 111 * | 99 * | 93 * | 74 * | 62 * | 31 | 12 |
| | 0.30 | 105 * | 95 * | 84 * | 79 * | 63 * | 53 * | 26 | 11 |
| | 0.35 | 92 * | 83 * | 74 * | 69 * | 55 * | 46 * | 23 | 9 |
| | 0.40 | 82 * | 74 * | 66 * | 62 * | 49 * | 41 * | 21 | 8 |
| | 0.45 | 74 * | 67 * | 59 * | 56 * | 45 * | 37+ | 19 | 7 |
| | 0.50 | 68 * | 61 * | 55 * | 51 * | 41 * | 34 | 17 | 7 |
| | 0.55 | 63 * | 57 * | 50 * | 47 * | 38+ | 32 | 16 | 6 |
| | 0.60 | 59 * | 53 * | 47 * | 44 * | 35 | 29 | 15 | 6 |
| | 0.65 | 55 * | 50 * | 44 * | 41 * | 33 | 28 | 14 | 6 |
| | 0.70 | 52 * | 47 * | 42 * | 39+ | 31 | 26 | 13 | 5 |
| | 0.75 | 49 * | 44 * | 39+ | 37 | 30 | 25 | 12 | 5 |
| | 0.80 | 47 * | 42 * | 38 | 35 | 28 | 24 | 12 | 5 |
| | 0.85 | 45 * | 40 * | 36 | 34 | 27 | 22 | 11 | 4 |
| | 0.90 | 43 * | 39 | 34 | 32 | 26 | 22 | 11 | 4 |
| | 0.95 | 41 * | 37 | 33 | 31 | 25 | 21 | 10 | 4 |
| | 1.00 | 40 * | 36 | 32 | 30 | 24 | 20 | 10 | 4 |

The values marked with * illustrate the range in a theoretical observation of the combinations of $g_i$ and x, for which no acceleration arises with respect to a conventional PCR with $g_h \approx 100\%$.

Example 2

This example is based on Example 1 and includes the case in which the cycle duration $t_{c_i}$ according to the invention is preferably selected to be shorter than the conventional cycle duration $t_{c_h}$, but furthermore in such a way that the yield per cycle can remain approximately the same as in the case of the selection of the cycle duration to date $t_{c_h}$, i.e. $g_i \sqrt{g_h}$ (this can, e.g. make it necessary for the annealing and the elongation to continue in each cycle to run with approximately the same efficiency as when the cycle duration thus far $t_{c_h}$ is selected). In other words, here the efficiency loss factor y=1, as according to definition in this example no efficiency loss arises.

In this case the number of cycles necessary for a desired amplification can then remain constant, and the duration of each cycle can be shortened by the factor x and the process duration according to the invention can be shortened correspondingly to $T_i = T/x$. In other words: with the example values indicated in Table 2 the PCR duration of a hypothetical conventional PCR T can be read within the scope of this theoretical observation in the second column. The process duration for a PCR according to the invention with $g_{0i}$; $=g_0$ can then be read in the same line as the conventional comparative value.

In an example realization of these examples, the cycle duration is selected so that it continues to be greater than the required productive time $t_{ci}-t_{ti}\gg t_{pi}$, so that, e.g. approximately $g_i=g_h\approx 100\%$ is reached.

Example 3

This example is also based on Example 1. However, it is now assumed that the shortening of the example cycle duration $t_{ci}$ in comparison with the conventional cycle duration $t_{ch}$ leads to a reduction in the average yield per cycle $g_i$ in comparison with the average yield thus far $g_h$ $$\left(\text{i.e. the efficiency loss factor} = y = \frac{g_h}{g_i} > 1\right).$$

As further assumed, this decrease in the yield per cycle, which can result from the shortening of the cycle duration by factor x, but can be more than compensated through more temperature cycles (which can be carried out more quickly by the factor $$x = \frac{t_{ch}}{t_{ci}}\right),$$

i.e. the increase in the amplicon concentration per time unit is nevertheless higher (wherein the time unit under observation is preferably to be selected to be very much longer than $t_{ch}$).

A decrease in the average yield per cycle can be realised, e.g., by the cycle duration becoming even shorter than the required productive time, i.e. $t_{ci}<t_{pi}$, wherein $t_{pi}=t_{ph}$ remains, so that the yield per cycle is $g_h\gg 100\%$ (e.g. because only few copies of the template can hybridize in the time with a primer and/or the polymerase cannot, in the time, elongate all the primers or the denaturing does not take place completely, since, e.g., the duration of effect is so short that the DNA double strand cannot sufficiently unravel.

Example 3a

It is assumed in this example that the following relationship applies for the yield:

$$g_h \geq g_i \geq \frac{g_h}{x}. \tag{10}$$

In other words, the average yield per cycle increases in this embodiment preferably maximum linearly with the shortening x of the cycle duration, whereby this can arise for example if the cycle duration no longer suffices for a large part of the template DNA to be able to hybridize with a primer (i.e. the efficiency loss factor is here $1<y\leq x$). The decrease in the yield per cycle, which is maximum factor x, can thereby be more than compensated by x times more cycles per time unit. In this case it can be written as follows:

$$N_i \geq N_0\left(1+\frac{g_h}{x}\right)^{f_{c_h}\cdot x\cdot t} = N_0\left(\underbrace{\left(1+\frac{g_h}{x}\right)^x}_{:=\alpha}\right)^{f_{c_h}\cdot t} = N_0\cdot \alpha^{f_{c_h}\cdot t}. \tag{11}$$

In this case the basis of the exponential function a can be greater than in a conventional PCR, where the basis of the exponential function can be according to Equation (4) $(1+g_h)$ and, in the best case scenario, is equal to two. This is summarized in the following table, which contains values for $(1+g_h)$ and also for $\alpha$:

TABLE 3

Values for $\alpha$ in comparison with a hypothetical basis, thus far, of the exponential function $(1 + g_h)$.

| | Conventional $(1 + g_h)$ | 1.11 | 1.25 | 1.33 | 1.67 | 2.00 | 4.00 | 10.00 |
|---|---|---|---|---|---|---|---|---|
| $g_h$ 0.40 | 1.40 | 1.41 | 1.41 | 1.42 | 1.43 | 1.44 | 1.46 | 1.48 |
| 0.60 | 1.60 | 1.62 | 1.63 | 1.64 | 1.67 | 1.69 | 1.75 | 1.79 |
| 0.80 | 1.80 | 1.83 | 1.86 | 1.87 | 1.92 | 1.96 | 2.07 | 2.16 |
| 1.00 | 2.00 | 2.04 | 2.08 | 2.11 | 2.19 | 2.25 | 2.44 | 2.59 |

This means that the amplification taking place per time unit can be greater than conventionally, provided that $g_0>0$ and Equation 10 is fulfilled. The inventors therefore refer to the process according to the invention also as "super-amplification".

The time required by a PCR according to the invention in this embodiment is given if Equation 9 for the PCR duration is re-written to:

$$T_i \leq \frac{t_{c_h}}{x}\cdot \log_{(1+g_0/x)}\left(\frac{N}{N_0}\right). \tag{12}$$

In other words: In the example of Table 2 the PCR duration of a hypothetical conventional PCR can be read in the second column. In comparison with a conventional comparative value, the process duration according to the invention can then be read in an entry with values without * or + in the same line or above, depending on which value combination of $g_i$ and x is realised.

A particularly interesting variant of this embodiment results for conventional PCRs, wherein the yield per cycle $g_0\approx 100\%$ (lowermost line in Table 3).

In this case, $\alpha$ in Equation 11 can be approximately re-written as $$\alpha = \left(1+\frac{1}{x}\right)^x.$$

PIC. It can also be preferably achieved that x becomes very high, so that approximately the threshold formation $$\lim_{x\to\infty}\left(1+\frac{1}{x}\right)^x = e$$

is admissible ($e\approx 2.71828\ldots$), so that the value for $N_i$ can be approximated from Equation 11 as:

$$N_i\approx N_0\cdot e^{f_{c_h}t} \tag{13}$$

It is shown here, in comparison with Equation 6, that the time-based amplification can no longer take place with $$2^{f_{c_h} \cdot t},$$

but instead with $$e^{f_{c_h} \cdot t},$$

i.e. the basis of the exponential function can be greater.

From Equation 13, the process duration for the case in which x is very high, can be approximately estimated as $$T_i \approx \ln\left(\frac{N_i}{N_0}\right) t_{c_h}, \quad (14)$$

for which the fact that $f_{c_h}=1/t_{c_h}$ has again been utilized. In other words, in this case the process duration can go hand in hand with the natural logarithm of the amplification factor.

Example 3b

This example is also based on Example 1. Shorter temperature cycles can also be used in this embodiment. However, in this embodiment the shortening according to the invention of the cycle duration $t_{ci}$, with respect to the cycle duration $t_{ch}$ thus far, can lead to a reduction in the yield per cycle $g_i$ with respect to the yield $g_h$ thus far, so that the following can apply:

$$\frac{g_h}{x} > g_i, \quad (15)$$

This means that the yield per cycle in this embodiment can decrease more than linearly with the shortening x of the cycle duration (i.e. the efficiency loss factor is here y>x). Also in this case, the decrease in the yield per cycle can be preferably overcompensated by more cycles, which are carried out more quickly than conventionally by the shortening factor x under suitable conditions.

In the example of Table 2 the hypothetical process duration of a conventional PCR can be read in the lowermost entry of the second column for $g_h \approx 100\%$ (in this case therefore: the value 40). The process duration in this embodiment of the invention can then be read in the entries, of which the values are marked with a +, provided that this value combination of $g_i$ and x can be realized.

FIG. 1 shows an exemplary embodiment of the method according to the invention for the amplification of nucleic acids 1, which is carried out as a PCR. First nanoparticles 3 are contained in a reaction volume 2. The first nanoparticles 3 have oligonucleotides 4 at their surface, as shown in FIG. 1a. One class of oligonucleotides 4 contain, in each case as a sub-sequence, a primer sequence 5 with the sequence A and, as a further, optional sub-sequence, a spacer sequence 6 S and an optional abasic modification 7 between the primer sequence 5 A and spacer sequence 6 S. The primer sequence 5 thereby serves as a forward primer 8. The spacer sequence 6 S is used to keep the primer sequence 5 far enough away from the surface of the nanoparticles 9 so that a nucleic acid 1 to be amplified can bind with better efficiency to the primer sequence 5 and a DNA polymerase 11 can find better access to the primer sequence 5. The abasic modification 7 prevents the spacer sequence being overwritten by the polymerase 11. The oligonucleotides 4 with the primer sequence 5 A are, e.g., fixed with a thiol bound to the surface of the first nanoparticles 3, so that the 3'-end faces away from the first nanoparticle 3. Optionally, a further class of oligonucleotides 4 can be located on the surface of the first nanoparticles 3, these are the filling molecules 10 F. With the filling molecules 10 the charge of the nanoparticles 9 can be modulated so that undesired aggregations of the nanoparticles 9 do not arise. In addition the filling molecules 10 can increase the distance of the primer sequences 5 from each other on the surface of the nanoparticles 9, so that the nucleic acids 1 to be amplified and the DNA polymerase 11 have better access to the primer sequences 5. This can increase the efficiency of the method. The spacer sequence 6 is thereby preferably at least as long as the filling molecules 10, so that the primer sequences 5 advantageously project out of the filling molecules 10.

In the reaction volume 2 there is a liquid sample 12, which contains the first nanoparticles 3 of FIG. 1a with the primer sequences 5, spacer sequences 6, abasic modification 7 and filling molecules 10, and which also has dNTPs and DNA polymerase 11. A nucleic acid 1 to be detected can be present in the sample 12. In this exemplary embodiment the nucleic acid 1 to be detected is a DNA single strand, which is also described as an original 13 or amplicon, and has a sub-sequence A' and also a sub-sequence B'. The original 13 can also have further sub-sequences, e.g. as overhangs at the 5'-end or 3'-end or between the two sub-sequences A' and B'. In FIG. 1b, the original 13 with its sub-sequence A' binds to the primer sequence 5 A on the surface of the first nanoparticles 3. It is shown in FIG. 1c that a DNA polymerase 11 binds to the original 13 and the primer sequence 5 A hybridized with the original 13. Then, the DNA polymerase 11 synthesizes, in an elongation step shown in FIG. 1d, starting from the 3'-end of the primer sequence 5 A, a nucleic acid 1 that is complementary to the original 13 and is referred to as a complement 14 and is combined with the spacer sequence 6 on the surface of the first nanoparticle 3. In FIG. 1e, the first nanoparticle 3 is then irradiated with light, which is absorbed by the first nanoparticle 3 due to its plasmonic or material properties and is converted into heat. The heat is emitted to the environment of the first nanoparticle 3 and, in the area of the original 13 and the newly synthesized complement 14 hybridized with it, the heat is sufficient for the original 13 to denature from the complement 14. The original 13 is now free again, as shown in FIG. 1f, so that it can bind to a further primer sequence 5 and further nanoparticle-bound complements 14 can be synthesized in further cycles of the method. This produces a linear increase in the concentration of the complements 14 with an increasing number of cycles.

In one embodiment of the method, after the extension of the primer sequence 5 on the surface 4 of the first nanoparticles 3, wherein a nanoparticle-bound complement 14 is produced, a free reverse primer 15 is used, which binds to the 3'-end of the complement. It is shown in FIG. 1g that the already synthesized complement 14 with the sub-sequences A and B, which is combined via a spacer sequence 6 and an abasic modification 7 on the surface of the first nanoparticle 3, hybridizes with a reverse primer 15 B' that was previously free in the sample 12. The primer 8 has the sequence B' and is combined with the sub-sequence B of the complement 14. Starting from the primer 8 with the sequence B', the DNA polymerase synthesizes a copy of the original 13. The synthesis takes place only up to the abasic modification 7, as this cannot be overwritten by the polymerase 11. It is also shown in FIG. 1g that the original 13 has bound to a further primer sequence 5 A on the surface of the first nanoparticle 3 and a DNA polymerase 11 starting from the primer sequence 5 A synthesizes a further complement 14. The original 13, the copy of the original 13 and the two complements 14 combined with the first nanoparticle are shown in FIG. 1h. A subsequent denaturing through excitation of the first nanoparticles 3 leads to the original 13 and its copy becoming free. Both the original 13 and also its copy can thereby serve in subsequent steps of the method as a template for amplification. After a waiting period, which is possibly necessary for the hybridization of the original 13 and copies of the original 13 with primer sequences 5 A on the first nanoparticles 3 and free primers 8 B' with primer sequences 5 already elongated on the first nanoparticles 3, the next cycle of the method can be carried out with a further excitation of the first nanoparticles 3. The cycle is preferably repeated until a sufficient number of extended primer sequences 5 are located on the first nanoparticles 3 and/or a sufficient number of copies of the original 13 are located in the sample 12, in order to be able to carry out a detection of the completed amplification or the presence of the original 13 in the sample 12. Through a free primer 8 B', as shown in FIGS. 1g and 1h, an exponential amplification of the original 13 is possible. In FIGS. 1a to 1f, without this free primer 8, however, only a linear amplification of the nanoparticle-bound complement 14 can be achieved.

Figure 2:
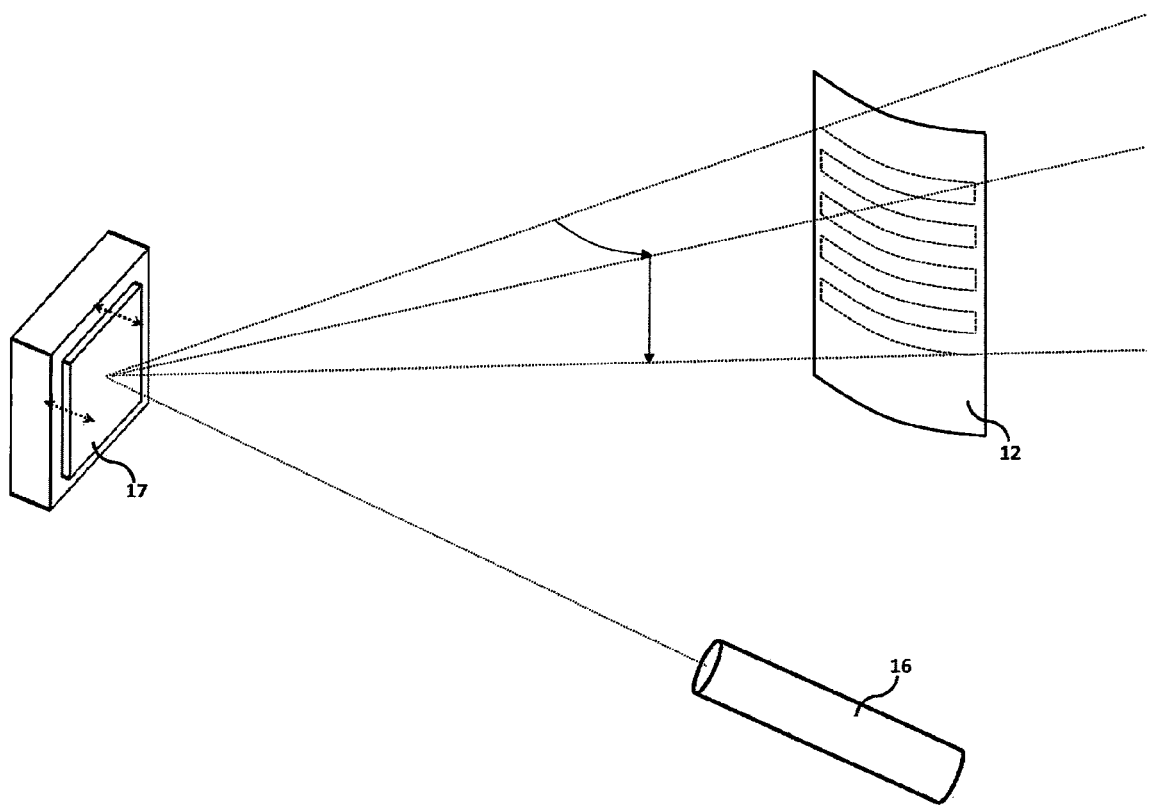
FIG. 2 shows in a schematic illustration a structure for carrying out the method according to the invention with a laser, a two-dimensional mirror scanner and a sample.

FIG. 2 shows a structure that is suited for carrying out the method according to the invention. The structure contains a light source, which is implemented in this example as a laser 16, and a two-dimensional mirror scanner 17, which can guide light from the laser 16 to the sample 12. The two-dimensional mirror scanner 17 can thereby deflect the laser beam in two dimensions. The denaturing in the sample 12 takes place in this structure in that a laser beam is focussed on a part of the sample 12. In the course of the method the laser beam is deflected so that it impinges on different parts of the sample 12. In the example shown in FIG. 2, the laser beam is deflected by the mirror scanner 19 in such a way that the laser beam travels linearly over the reaction volume 2, in which the sample 12 is located. The path covered by the laser beam is shown in dotted lines in FIG. 3 in the sample 12. Due to the fact that at each time point of the method only parts of the sample 12 are excited, lasers 16 with a lower power can be used. As excitations of less than a microsecond suffice in order to denature DNA with the aid of optothermally heated nanoparticles 9, in the case of typical focus diameters of a laser 16 from approximately 10 to 100 µm, a laser beam with a speed of approximately 10 to 100 m/s can scan the sample 12 and thereby lead to a denaturing of the DNA at each point over which the laser beam travels. This facilitates a very rapid scanning also of large sample volumes. The complete scanning of a surface area of 1 cm² takes only 128 ms, e.g. with a focus diameter of 78 µm and 128 lines at a line distance of 78 µm and a line length of 1 cm, with a speed of the scanning laser beam of 10 m/s. If the volume has e.g. a depth of 10 mm, a volume of 1 ml can be processed (for this it must of course be ensured, inter alia, that the intensity of the excitation is sufficiently high over the whole depth). This is advantageously substantially shorter than would generally be required by a denaturing step through global heating. With optical elements such as e.g. a mirror scanner 17 shown in FIG. 2, and so-called F theta lenses, a good homogeneity of the focus quality and size can be achieved over the whole scanned sample 12. Alternatively to a continuously emitting laser 16, a pulsed laser 16 or a thermal radiator can also be used.

Figure 3:
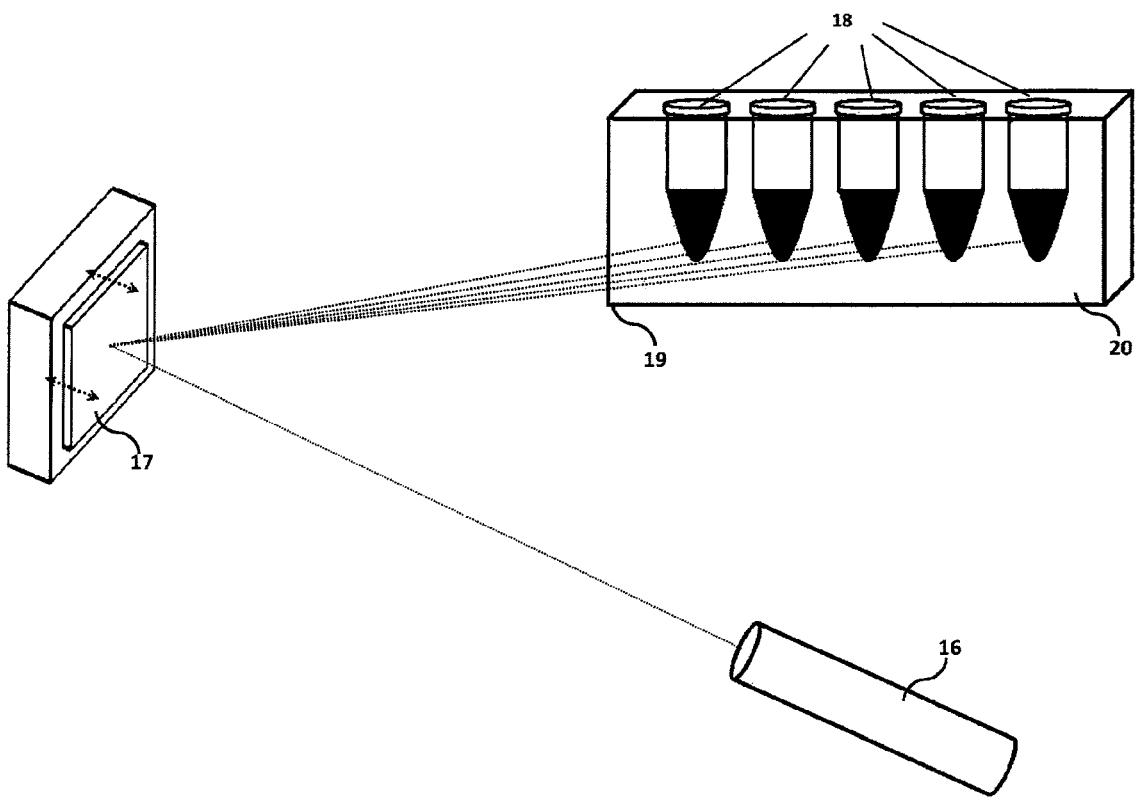
FIG. 3 shows in a schematic illustration a further structure for carrying out the method according to the invention with a laser, a two-dimensional mirror scanner and sample tubes in a water bath.

In the embodiment of the method shown in FIG. 1, first nanoparticles 3 of gold with a diameter of 60 nm are functionalized with oligonucleotides 4 ID1 (according to J. Hurst et al., Anal. Chem., 78(24), 8313-8318, 2006, the related content of which is part of the present disclosure by virtue of reference thereto). After functionalization and 6 washing steps, the first nanoparticles 3 are present in a concentration of 200 pM in a PBS buffer (5 mM PBS, 10 mM NaCl, 0.01% Tween 20, pH 7.5). The amplification reaction is carried out in a total volume of 10 µl in 100 µl sample tubes 18 (2 µl Apta Taq Mastermix 5× with MgCl2 (obtained from Roche), 1 µl NaCl 450 mM, 1 µl MgCl$_2$ 90 mM, 1 µl Tween 20 1%, 2 µl water, 1 µl of the functionalized first nanoparticles 200 pM, 1 µl oligonucleotide 4 ID2 5 µM as a dissolved reverse primer and 1 µl oligonucleotide ID3 as original 13 to be amplified). The concentration, to be determined, of the original 13 in the total volume of 10 µl, e.g. 0.1 fM of the oligonucleotide ID3 dissolved in water with 100 nM oligonucleotide 4 ID4 (oligonucleotide ID4 hereby serves for the saturation of surfaces, e.g. during the maintenance of the original 13 before the reaction.) As shown in FIG. 3, the sample tubes 18 are brought in a glass cuvette 19 in a water bath 20 to a temperature of 64° C., which constitutes both the annealing temperature and the elongation temperature. The water bath 20 serves, besides tempering, also for improved introduction of the laser 16 into the non-planar surface of the sample tubes 18. The water in the water bath 20 allows the refractive index difference between the outside and the inside of the sample tubes 18, filled with PCR reaction mix, to be reduced and to therefore prevent a refraction of the laser beam and hence a negative influence on the focus quality and sharpness. The coupling of the laser 16 is thereby advantageously improved. The laser 16 which is used to excite the nanoparticles is a frequency-doubled diode-pumped Nd:YAg-Laser (CNI Lasers Inc.), which is focused, with an output power of 2.5 W with a F-Theta lens (Jenoptik, focal length 100 mm) behind a mirror scanner 17 (Cambridge Technologies, Pro Series 1) into the sample tubes 18 in the water bath 20 (focus diameter approximately 20 µm). The mirror scanner 17 allows the focus to move line by line through the sample tubes 18, as also already shown in FIG. 3, and thus allows the whole PCR reaction volume to participate in the optothermal amplification. For each sample tube 18, 680 lines with a distance of approximately 12 µm, with a line speed in the sample tubes 18 of approximately 10 m/s, are covered with the focus. This corresponds to a cycle in the first sample tube 18. Subsequently all other sample tubes 18 are travelled over one after the other, so that each sample tube 18 has undergone a cycle. After a waiting period, which can be selected differently in each sample tube 18, the next cycle is started. This is repeated as often as needed with differences for each sample tube 18.

Figure 6:
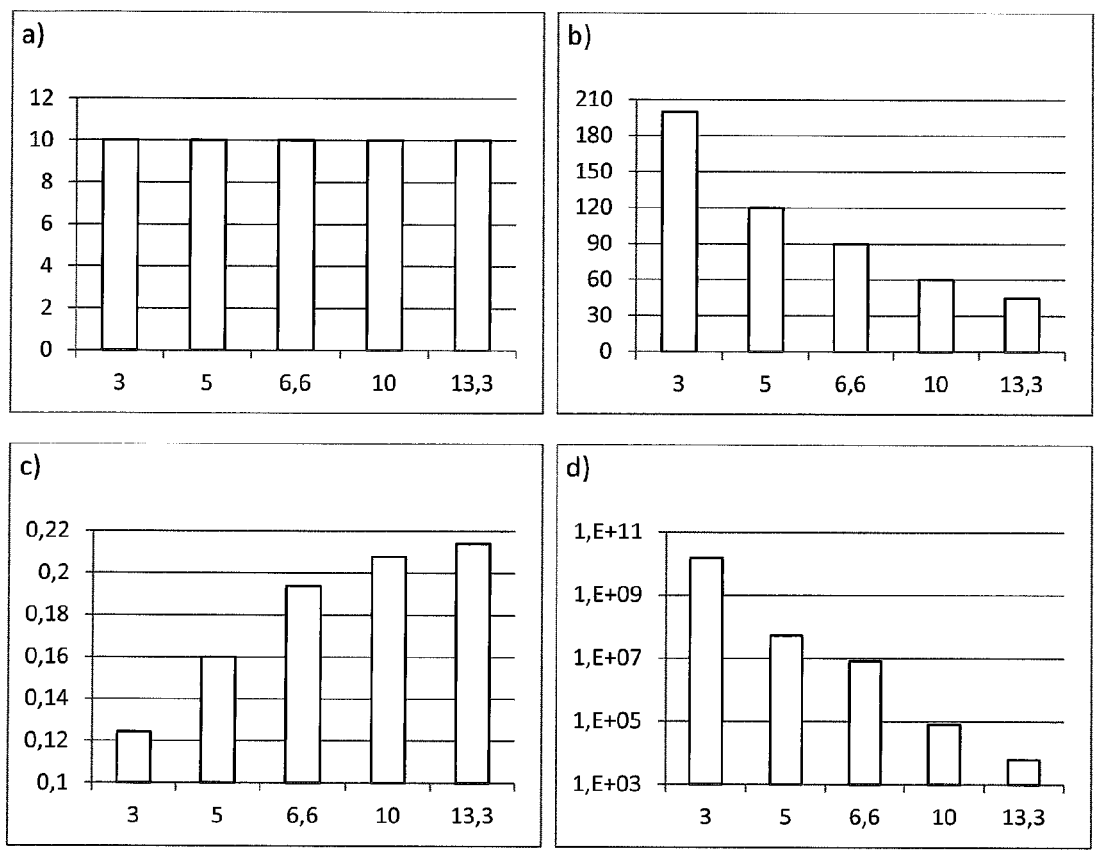
FIG. 6 shows in four diagrams the results of amplification reactions with different cycle times and numbers of cycles.

FIG. 6 shows data for five different sample tubes, which contain as a starting concentration of the original 103 in each case 0.1 fM. In the first sample tube a total of 200 cycles are carried out with a waiting time of 3 s between the individual cycles, in the second sample tube 120 cycles at 5 s, in the third sample tube 90 cycles at 6.6 s, in the fourth sample tube 60 cycles at 10 s and in the fifth sample tube 45 cycles at 13.3 s. This is shown in FIG. 6b. The script below the diagrams indicates in each case the waiting time. The total duration from the first to the last cycle is 10 minutes in each of the five sample tubes. This is shown in FIG. 6a. In order to determine the total amplification through the optothermal amplification reaction, after the end of the amplification reaction 1 µl of the sample is removed from each sample tube and diluted in 99 µl water. From this dilution or thinning, 1 µl is introduced into an amplification reaction to be quantified (real-time PCR) in order to determine the concentration of the copies of the original there that were produced in the different sample tubes by the optothermal amplification reaction. This dilution serves for possibly inhibiting or interfering content substances from the optothermal amplification reaction being diluted too greatly, so that they can no longer interfere in the subsequent quantifying amplification reaction. The quantifying amplification reaction is performed in a LightCycle II (Roche). Here, there is a cycle of 10 s denaturing at 94° C., 10 s annealing at 62° C. and 10 s elongation at 72° C. At the end of the 72° C. step, the measurement of the fluorescence is also carried out. Prior to the start of the first cycle, a once-only denaturing step takes place at 94° C. for 30 s. Besides 1 µl of the diluted copies of the original from the optothermal amplification reaction, 10 µl reaction volume for the quantifying amplification reaction contains 2 µl Apta Taq Mastermix 5× with $MgCl_2$ (obtained from Roche), 2.8 µl water, 2 µl oligonucleotide 4 ID5 1 pM as dissolved forward primer, 2 µl oligonucleotide 4 ID6 1 µM as a dissolved reverse primer and 0.2 µl SYBRGreen 100× as intercalating colour dye in order to make the PCR product detectable during the real-time PCR. An additional standard curve, which is determined with a diluting or thinning series of known concentrations of oligonucleotide 103 as original for the quantifying amplification reaction, allows the subsequent quantification of the copies used into the quantifying amplification reaction. The total amplification is thereby determined that was produced during the optothermal amplification reaction in the different sample tubes. This is shown in FIG. 6d. It can clearly be seen here that the total amplification, despite equal process time (in each case 10 minutes, see FIG. 6a), with increasing cycle duration (and thereby decreasing number of cycles), greatly decreases. Assuming that over the whole amplification reaction the amplification factor per cycle remains constant, the yield per cycle g can be calculated from Equation (2). The thus determined g is shown in FIG. 6c. It can clearly be seen here that g increases with increasing cycle duration. Despite the decreasing g with decreasing cycle duration, the total amplification with the same process duration increases with decreasing cycle duration.

Figure 4:
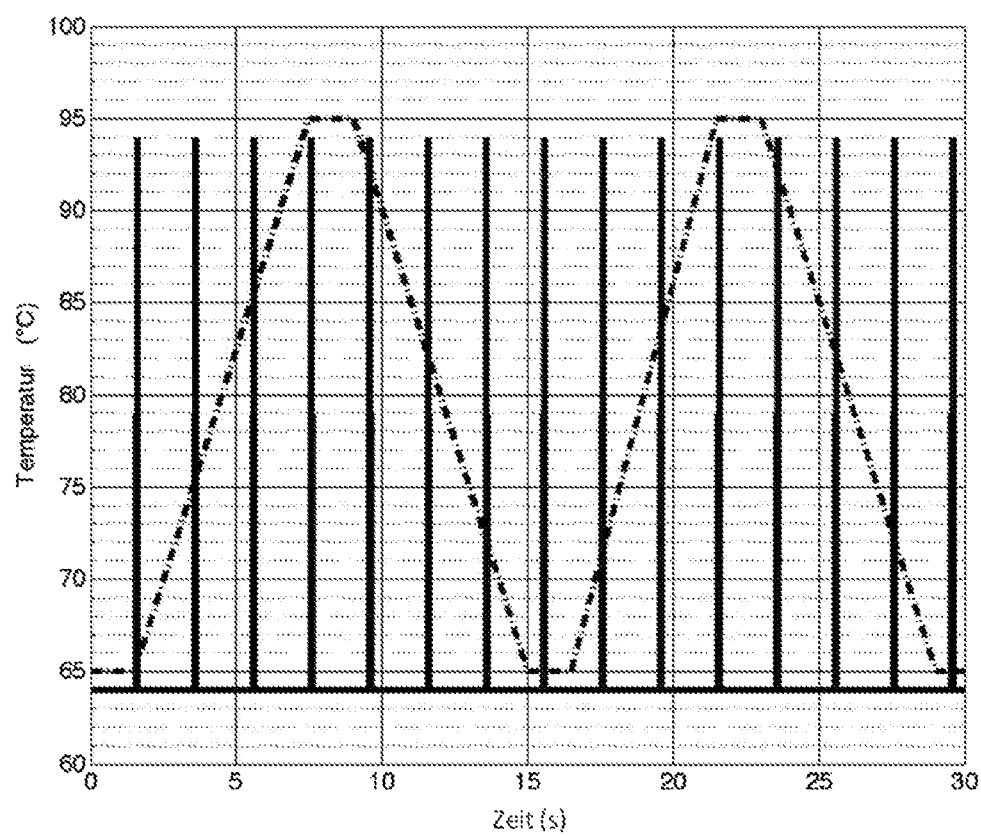
FIG. 4 shows the idealized temperature profile of a conventional PCR (dotted line)

FIG. 4 shows the idealized temperature profile of a conventional PCR (dotted line) with a cycle duration of $t_A$, =15 s. A constant slope of 5 K/s was assumed for the temperature flanks. In contrast, one embodiment of the PCR method according to the invention, with a cycle duration $t_{ch}$=2 s, is shown with a constant slope of the temperature flanks of 3000K/s, as can be achieved for example through optical excitation of nanoparticles according to the invention (solid line; for better legibility, the temperature profile was displaced by 1° C. downwards).

Figure 5:
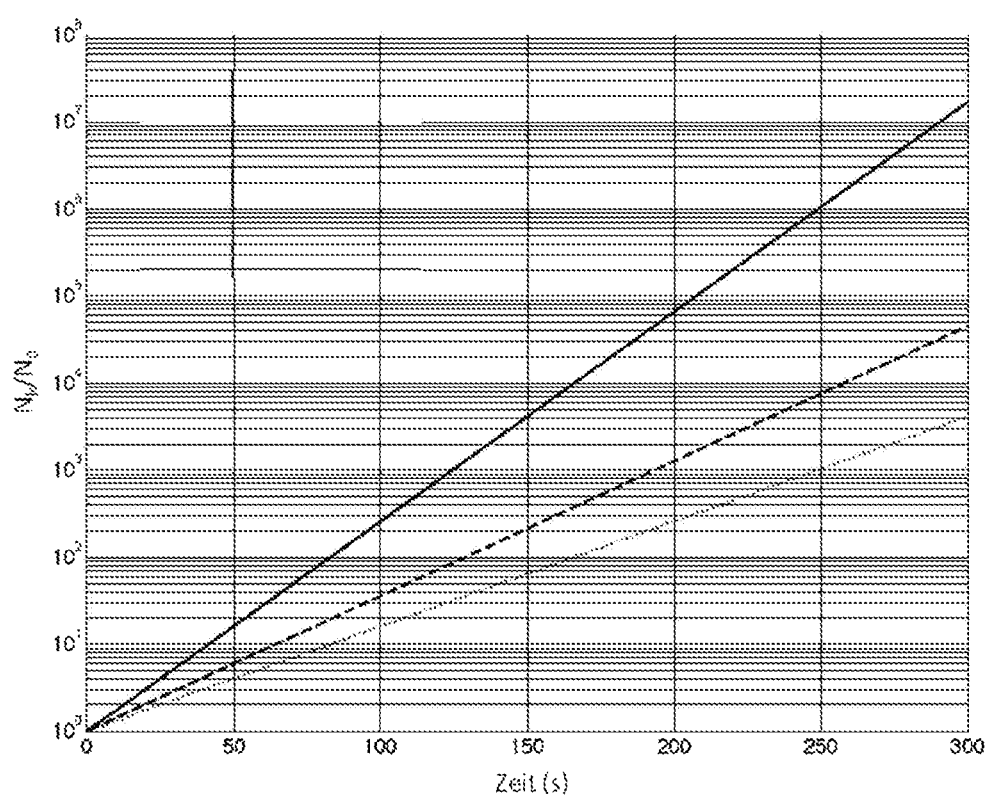
FIG. 5 shows the amplification factor $N_k/N_o$ as a function of the time for different parameters.

FIG. 5 shows the amplification factor $N_k/N_0$ as a function of the time for different parameters. The pointed line shows the amplification of a typical conventional PCR with a cycle duration of $t_{ch}$=25 s and a yield per cycle of $g_h$=100%. The dotted line shows the amplification in a preferred conversion according to the invention with
$g_t$=25%, x=4

$$t_{c_i} = \frac{t_{c_h}}{x} = 6,25s$$

The solid line shows another preferred conversion according to the invention with $g_i$=100%, x=2 and $$t_{c_i} = \frac{t_{c_h}}{x} = 12,5s$$

The features disclosed in the above description, the claims and the drawings can be significant both individually as well as in any combination for the realisation of the invention in its different embodiments.

REFERENCE SYMBOL LIST

1 Nucleic acid
3 Reaction volume
3 First nanoparticles
4 Oligonucleotide
5 Primer sequence
6 Spacer sequence
7 Abasic modification
8 Forward primer
9 Nanoparticle
10 Filling molecule
11 DNA polymerase
12 Sample
13 Original; amplicon
14 Complement
15 Reverse primer
16 Laser
17 Mirror scanner
18 Sample tube
19 Glass cuvette
20 Water bath

The invention claimed is:

1. A method for amplifying nucleic acids by means of a polymerase chain reaction, the method comprising performing a denaturing step, an annealing step and an elongation step, wherein a cycle consisting of: the denaturing step, the annealing step and the elongation step is performed repeatedly on at least one nucleic acid, wherein the yield (g) of specimens of the nucleic acid to be amplified, at the end of at least one of the passages of the cycle, is less than 80 percent of the specimens of the nucleic acid present at the start of this passage of the cycle, and that in at least one of the passages of the cycle a duration of effect ($t_A$) is shorter than one second.

2. The method of claim 1, wherein the number (k) of the passages of the cycle of the polymerase chain reaction is greater than 45.

3. The method of claim 1, wherein the concentration of the amplicon to be amplified in the method is less than 1 nM at the start of the method.

4. The method of claim 1, wherein the cycle duration $t_c$ is shorter than 20 seconds in at least one of the passages of the cycle.

5. The method of claim 1, wherein nanoparticles in a reaction volume transfer heat to their environment through excitation.

6. The method of claim 5, wherein a heating time in at least one of the passages of the cycle is shorter than 10 ms.

7. The method of claim 5, wherein a cooling time in at least one of the passages of the cycle is shorter than 10 ms.

8. The method of claim 5, wherein a power density, with which the nanoparticles are excited, is more than 10 W/mm$^2$.

9. The method of claim 5, wherein a power density, with which the nanoparticles are excited, is less than 20,000 kW/mm$^2$.

10. The method of claim 5 wherein through the excitation of the nanoparticles the environment of the nanoparticles is locally heated.

11. The method of claim 5 wherein the nanoparticles are excited by a laser.

12. The method of claim 5 wherein the nanoparticles are conjugated to oligonucleotides.

13. The method of claim 12 wherein, in one class of the conjugates of nanoparticles and oligonucleotides, the nanoparticles are conjugated with oligonucleotides both in the form of forward primers and reverse primers.

14. The method of claim 12 wherein in the method counter-sequences are used, which can combine with oligonucleotides that have detached from the nanoparticles, with which they were previously combined.

* * * * *